(12) United States Patent
Tamura et al.

(10) Patent No.: US 6,605,639 B1
(45) Date of Patent: Aug. 12, 2003

(54) LIGANDS OF NUCLEAR RECEPTOR

(75) Inventors: Gakuzo Tamura, Tokyo (JP); Kunio Ando, Kanagawa (JP); Junji Magae, Ibaraki (JP); Takafumi Uchida, Kanagawa (JP)

(73) Assignee: Nuclear Receptor Research, Ltd., Kanagawa (JP)

( * ) Notice: Subject to any disclaimer, the term of this patent is extended or adjusted under 35 U.S.C. 154(b) by 0 days.

(21) Appl. No.: 09/868,059

(22) PCT Filed: Dec. 14, 1999

(86) PCT No.: PCT/JP99/07012

§ 371 (c)(1),
(2), (4) Date: Jun. 14, 2001

(87) PCT Pub. No.: WO00/35867

PCT Pub. Date: Jun. 22, 2000

(30) Foreign Application Priority Data

Dec. 14, 1998 (JP) ............................................. 10-377905

(51) Int. Cl.⁷ ........................ A01N 37/10; A01N 35/00; A61K 31/12; C07C 49/76
(52) U.S. Cl. ........................ 514/543; 514/569; 514/683; 514/824; 514/825; 514/866; 514/885; 568/329
(58) Field of Search ................................. 514/543, 569, 514/683, 824, 825, 866, 885; 568/329

(56) References Cited

U.S. PATENT DOCUMENTS 3,995,061 A * 11/1976 Hosokawa et al.
4,542,143 A * 9/1985 Hosokawa et al.

FOREIGN PATENT DOCUMENTS

| EP | 74628 | 3/1983 |
|---|---|---|
| GB | 1495353 | 12/1977 |
| JP | 51110035 | 9/1976 |
| JP | 3291220 | 12/1991 |
| WO | 93/21146 | 10/1993 |
| WO | 94/05274 | 3/1994 |
| WO | 94/15902 | 7/1994 |
| WO | 94/17796 | 8/1994 |
| WO | 95/04036 | 2/1995 |
| WO | 96/13478 | 5/1996 |
| WO | 97/10819 | 3/1997 |

OTHER PUBLICATIONS

Nature (London), vol. 386, No. 6623, (1997) Ranjan Mukherjee et al., pp. 407–410 Sugiyama Takuya et al., vol. 130 No. 6 (Jun. 1998) No. 10218 pp. 551–557.

* cited by examiner

*Primary Examiner*—Samuel Barts
*Assistant Examiner*—Sikarl A. Witherspoon
(74) *Attorney, Agent, or Firm*—Birch, Stewart, Kolasch & Birch, LLP

(57) ABSTRACT

It has been newly found out that ascochlorin, which is a publicly known fat-soluble antibiotic, and its homologues serve as a ligand of retinoid X receptor and react in vivo with the amino group of serum protein to form Schiff bases without showing any side effect of retinoid. Ascochlorin and its homologues are usable in treating and/or preventing a disease or condition which can be relieved by the retinoid X receptor ligand-dependent gene transcriptional regulation (for example, diseases caused by the expression of insulin resistance, hypertension, cerebrovascular diseases, rheumatoid arthritis, autoimmune disease, Ca metabolic disorder, complication of diabetes, arteriosclerosis, etc.). Moreover, they can inhibit denaturation and/or necrosis of pancreatic Langerhans islet β-cells and, therefore, are usable in making these cells to sustain the insulin productivity.

13 Claims, 8 Drawing Sheets

Fig. 3:

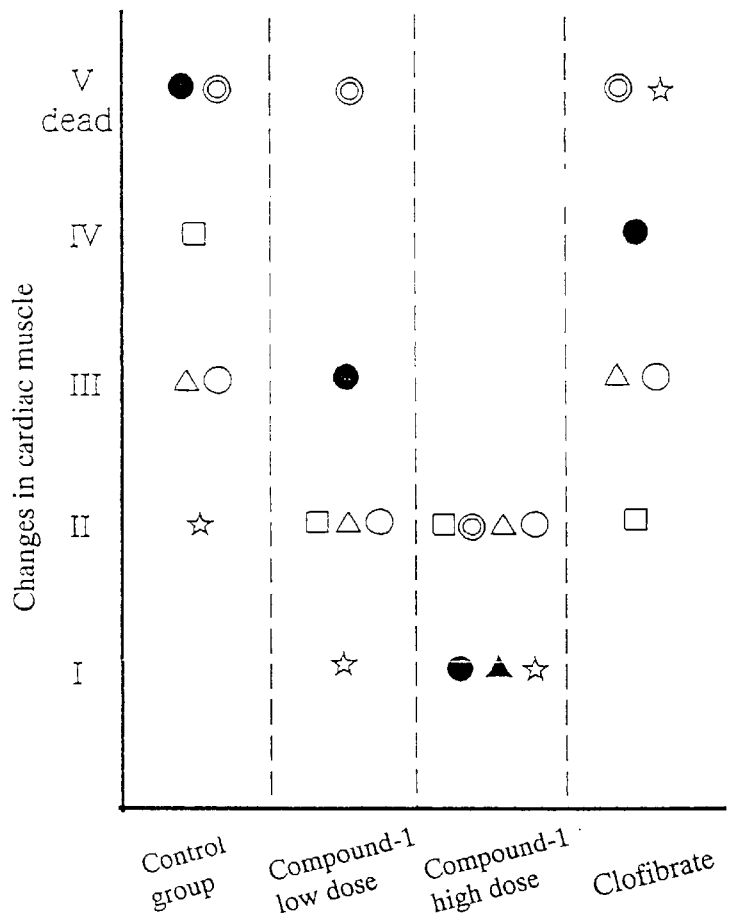

Grade I: slight denaturation and slight change into yellow in aorta and pulmonary artery origin.
Grade II: moderate denaturation and change into yellow to yellowish brown in aorta and pulmonary artery origin.
Grade III: severe denaturation, change into yellow to yellowish brown in aorta and pulmonary artery origin and change into yellow in one of cardiac papilla muscles.
Grade IV: very severe degeneration/necrosis, change into yellow to yellowish brown in aorta and pulmonary artery origin and degeneration/necrosis in both cardiac papilla muscles.
Grade V: death from arteriosclerosis caused by circulatory failure.

Mother's no.: ○ 608, ● 678, △ 697, ☆ 557, □ 558, ◎ 795

*P<0.005, P<0.025, *P<0.01 and ****P<0.005
No. of patients: 5 (all males), restricted to those showing fasting blood glucose level higher than 100 mg/dl.

**P<0.01 in Student paired t-test
No. of patients: 17 (8 females and 9 males)

No. of cases: 17, ***P<0.001 in Student's t-test
Dose of Compound-6: 360 mg/day divided into 3 portions and taken after each meal. No concomitant drug.

No. of cases: 7, *P<0.04 and **P<0.01 in Student's t-test
Dose of Compound-6: 360 mg/day divided into 3 portions and taken after each meal. No hypotensive drug.

Rats: male Wistar rats weighing 200 g (n = 4).
Mean ± SE.

LIGANDS OF NUCLEAR RECEPTOR

This application is the national phase under 35 U.S.C. §371 of PCT International Application No. PCT/JP99/07012 which has an International filing date of Dec. 14, 1999, which designated the United States of America and was not published in English.

TECHNICAL FIELD

This invention relates to ligands of retinoid X receptor and pharmaceutical compositions for treating and/or preventing diseases which can be alleviated by the retinoid X receptor ligand (RXRL)-dependent transcriptional regulation of certain genetic information.

BACKGROUND ART

Diseases to be treated and/or prevented by use of the pharmaceutical compositions according to the present invention involve life-style related diseases. From the viewpoint of treating the life-style related diseases, there is an urgent need to develop drugs for use in the treatment of various vascular lesions causative of the onset of the life-style related diseases. Ischemic heart disease, which is prevalent when vascular lesions are present, is also referred to as coronary sclerosis. It is thought that around fifty percent of all deaths in the world are attributable this disease. Ischemic heart disease is the leading cause of death in most developed countries, and the second biggest cause of death in Japan. In addition it is estimated that the incidence of ischemic heart disease will rapidly increase in developing countries also. Major causes of ischemic heart disease, appear to include genetic factors, eating habits, stress, diabetes and hypertension. It is known that ischemic heart disease is closely related to life-style including diet. Hyperlipemia and hyperinsulinemia, which are induced by the excessive intake of high caloric diets, promote sedimentation of low density lipoproteins which are rich in cholesterol on the arterial wall. Degeneration of sedimented low density lipoproteins causes damage to the arterial wall; and leukocytes react to the damage in the arterial wall and infiltrate it to repair the lesion, resulting in chronic inflammation. Thus the mechanism of arteriosclerosis is understood to be as follows: In response to damage of arterial wall, leukocytes, which attempt to repair the damage, cause excessive inflammation which has the effect of thickening the arterial wall, resulting in a sclerosing lesion.

Typical examples of known drugs for preventing ischemic heart disease are hydroxymethylglutaryl-CoA (HMG-CoA) reductase inhibitors. These HMG-CoA reductase inhibitors, which inhibit the biosynthesis of mevalonic acid as a rate-determining step in the biosynthesis of cholesterol, reduce the amount of cholesterol synthesized in the liver and thus lower the cholesterol content in the low density lipoprotein which is synthesized in the liver and released into the serum. That is to say, the main function of these drugs resides in inhibiting the biosynthesis of cholesterol and lowering the cholesterol content in the serum, thereby reducing the low density lipoprotein incorporated from the serum into the arterial wall depending on the concentration. Namely, these drugs exert a merely indirect and preventive effect. These HMG-CoA reductase inhibitors exhibit no effect on the sclerosing lesions associated with chronic inflammation which thickens the arterial wall in which macrophages and lymphocytes participate. Thus, it is impossible to achieve any direct therapeutic effect for healing chronic inflammation of an artery. An ideal remedy and/or preventive treatment for arteriosclerosis is a drug which shows an effect of lowering serum cholesterol level and, at the same time, a therapeutic and/or preventive effect on chronic inflammation induced by the sedimentation of cholesterol on the arterial wall. It is expected that such a drug, if any, would serve as an ideal remedy and/or preventive treatment for ischemic heart disease.

Similar to the coronary artery, the cerebral artery frequently suffers from lesions. When a cerebrovascular lesion proceeds, cerebrovascular lesions such as intracerebral bleeding or cerebral infarction are induced. Once a cerebrovascular lesion has occurred, there frequently result serious consequences such as movement disorder or intellectual disorder, even though death may be avoided. In a society where the population is aging, an increase in bed-ridden persons or persons suffering from senile dementia gives rise to serious social problems, and thus there is an urgent need to prevent these problems from the viewpoint of relieving the social burden of medical expenses, also. In Japan, the number of persons suffering from dementia caused by cerebrovascular dementia (i.e., partial degeneration and/or necrosis of the brain due to cerebrovascular lesions) amounts to almost 50% of the total number of persons suffering from dementia. Different from the coronary artery, the surface of the cerebral artery is coated with endothelial cells which closely overlap each other on the contact face. This coated state is referred to as tight junction. In the endothelium of the cerebral artery, endothelial cells are arranged closely without any voids. Therefore, low density lipoprotein is not incorporated into the arterial wall as in the heart. In other words, cholesterol will not induce arteriosclerosis in the cerebral artery. However, when the artery becomes enlarged due to hypertension and damage to the cerebral artery is caused, plasma components are able to penetrate the arterial wall. In response to such damage, leukocytes infiltrate the arterial wall, and as in the case of the coronary artery in the heart, the repair reaction becomes excessive. As a result, the cerebral arterial wall thickens whereby blood circulation disorders are caused; or the arterial wall becomes fragile as a result of chronic inflammation and fails to withstand blood pressure, whereby an aneurysm forms. When an aneurysm breaks, bleeding results, i.e., cerebral stroke. Thus, cerebrovascular lesion can be seen to result from chronic inflammation induced by the infiltration of leukocytes responding to repair small wounds in the artery, similar to coronary arteriosclerosis.

To prevent cerebrovascular lesions, hypotensive drugs have been employed exclusively. The effect of these hypotensive drugs resides in a lowering of blood pressure to protect vessels from excessive pressure, thereby preventing vascular damage. In other words, hypotensive drugs are employed as a preventative treatment to avoid negative effects consequent to (natural) repair of cerebral vessels. In Japan, there is a category of remedies for cerebrovascular dementia which are referred to as cerebral vasodilators, and it has been a practice to employ cerebral vasodilators such as idebenone, bifemelane hydrochloride, indeloxazine hydrochloride, nicergoline and propentofylline. As a result of clinical re-evaluation tests, however, it has been clarified that these drugs show no significant difference from placebos in therapeutic effect on negative consequences of cerebrovascular lesions. Accordingly, these drugs are no longer indicated for the treatment of the negative consequences of cerebrovascular lesions. Thus, it may be concluded that no remedy exists for the negative consequences of cerebrovascular lesions at the present time. It is expected that a drug having a hypotensive effect as well as a therapeutic effect on chronic inflammation of the cerebral artery, if any are present, would serve as an ideal remedy for cerebrovascular lesions.

As discussed above, it has been revealed that vascular lesions such as arteriosclerosis and aneurysm are induced by the repair of damage to the artery. It is known that arteriosclerosis is caused by damage to the arterial wall in a case where a narrowed artery is enlarged by inserting a balloon or a stent into it, or T lymphocytes of a host undergo a rejection reaction against an isoantigen which is present in the artery of a transplanted organ; in addition to chemical stimulus by, for example, a harmful degenerated agent such as degenerated low density lipoproteins, or under the physical stimulus of hypertension.

As examples of physical factors causative of arteriosclerosis, a treatment of inserting a balloon or a stent into a narrowed part of a coronary artery to enlarge a narrowed section (i.e., percutaneous angioplasty) may be cited. Due to its convenience and immediate effect, this treatment for enlarging physically a narrowed inner cavity of a coronary artery has been carried out at a frequency of 1,000,000 cases per year across the world since 1996. Since the inner cavity of a narrowed part of the artery is enlarged immediately by applying a physical force, the artery is damaged, with the result that leukocytes responsive to such damage infiltrate the area in an excessive repair reaction. It is known that thickening of the arterial wall at the enlarged part arises within 6 months in about 40% of patients in the case of enlargement with a balloon catheter, while re-constriction arises within 6 months in 20 to 40% of patients in the case of enlargement with a stent. In the case where re-constriction arises, it becomes necessary to perform percutaneous angioplasty once more or to perform coronary artery bypass to save life. That is to say, although percutaneous angioplasty is highly effective in rapidly enlarging an intraarterial cavity, no adequate means of preventing arteriosclerosis resulting from vascular damage due to enlargement of the intraarterial cavity has been found so far.

Arteriosclerosis caused by an immunological mechanism is typified by arteriosclerosis associated with organ transplantation. Relatively recently, T lymphocyte-specific immunosuppressants such as cyclosporin and tacrolimus have been developed, and thus acute rejections of transplanted organs within a year of transplantation can be suppressed almost completely. In heart, liver, kidney or cardiopulmonary transplantation, however, over 5 years in around 60% of cases transplanted organs remain accepted. Conversely, in about 40% of cases a phenomenon referred to as chronic rejection occurs. This phenomenon can be discriminated from acute rejection which occurs within one year following transplantation. Although the name "chronic rejection" is indicative that a transplanted organ has been rejected immunologically, it actually describes a condition where necrosis and drop-off of the transplanted organ occur as a result of circulatory disorders caused by arteriosclerosis. Chronic rejection is induced by damage which occurs as a result of immunological attack following recognition of an isoantigen in the artery of the transplanted organ by lymphocytes of the host. Then, leukocytes of the host in response to damage caused by the immunological attack react to repair the damage, thereby inducing arteriosclerosis. It has been clarified that chronic rejection correlates to the strength of an initial acute rejection. Namely, if an acute rejection is strong, the subsequent risk of the transplanted organ being lost within 5 years becomes high, as result of the artery of the transplanted organ being subject to more serious immunological damage. The reason is that arteriosclerosis is likely induced by an excessive repair reaction. If a means of regulating excessive chronic inflammation in an artery can be developed, chronic rejection can be halved in the case of organ transplantation. Thus, the background of the occurrence of arteriosclerosis has been illustrated.

The pharmaceutical compositions according to the present invention are aimed at treating type I diabetes and type II diabetes which are typical metabolic diseases. Type II diabetes is a life-style related disease, and closely correlates to obesity which, in turn, is dependent on both eating habits and genetic factors. In contrast, type I diabetes is a disease which arises when there is a lack in the overall amount of available insulin, which occurs when insulin-producing β cells are destroyed by an autoimmune reaction against pancreatic Langerhans' islet β-cells. Thus, administration of regular insulin injections is required to ensure the survival of patients with this disease. Although these diseases outlined above differ from each other in terms of cause, the complications of diabetes, which arise when the disease has been present for a long period of time, are common to both types. Diet therapy and exercise therapy are the major ways in which type II diabetes caused by the peripheral insulin resistance is treated, and drug therapy is employed merely an adjunct. In drug therapy, use is made of sufonylurea agents which accelerate insulin secretion from the pancreatic Langerhans' islet, and biguanide agents which promoting glucose utilization in peripheral tissue. However, there has been available no drug which is capable of activating peripheral insulin resistance which is causative of the onset of the disease. Thiazolidinedionediene (TZD) compounds developed recently have attracted attention as drugs having the ability to activate peripheral insulin resistance.

Several ten receptors referred to collectively as a nuclear receptor superfamily, which are known as receptors of fat-soluble hormones and vitamins, have been found in nuclei. In the course of studying the function of mechanism of synthetic organic TZD compounds, facts have been determined as follow: (1) the target tissue of these compounds are adipocyte tissue; (2) they are agonists specifically activating PPARα, a member of the nuclear receptor superfamily; and (3) they differentiate certain fibroblasts having been conditioned into adipocytes, at the cell culture level. After being activated by TZD, PPARγ forms a dimer (heterodimer) together with retinoid X receptor (RXR), which is also a nuclear receptor, and binds to a specific site (hormone recognition site) of chromosome thereby regulate the transcription of a definite gene. Based on experiments at the cell and tissue levels, it has been proved that the transcriptional regulation by this heterodimer contributes to the enhancement of the peripheral insulin sensitivity. That is to say, TZD activates PPARγ in adipocyte tissue dose-dependently and thus ameliorates the metabolic disorder in diabetes. Since there has been known no drug which acts on a gene and regulates the expression of a gene signal, it is it is to be expected that TZD would be so highly evaluated.

Since various ligands (for example, fatty acids, prostaglandins, nonsteroidal analgesic/anti-inflammatory agents) bind to the PPARγ receptor, the specificity of TZD to the PPARγ receptor is not necessarily high. Since the existing TZD compounds have a characteristic function of activating PPARα also and thus proliferating mammalian hapatocellular peroxisome thereby causing hepatic hypertrophy, it is doubted that these TZD compounds might relate to hepatopathy. Among them, troglitazone, which have been put into practical use for the first time among TZD compounds, causes hepatopathy in about 2% of patients at the normal dose and can cause death in extreme cases. Therefore, much attention needs to be paid in using such compounds from the viewpoint of safety. Provided that PPARγ agonists activate widely peripheral insulin resistance, these agonists must be considered useful not only in ameliorating metabolic disorder in diabetes but also in treating and/or preventing the complications of diabetes. However, on the basis of the results of animal experiments and clinical data on the TZD compounds, it cannot be concluded that the symptoms of insulin resistance syndrome and the complications of diabetes can be ameliorated significantly. Therefore, it there remains scope for improvement of TZD compounds, taking into consideration specificity of function, safety and usefulness.

On the other hand, it attention has drawn to what effect the RXR ligand forming a heterodimer together with PPARγ exerts on the metabolic disorder of type II diabetes. This is because PPARγ forms a heterodimer together with RXR and thus regulates the expression of the gene signal involved in the onset of diabetes. A first study suggesting a new direction for this problem was reported by researchers of Ligand, USA (Nature 386:407–410, 1997). According to thier report, retinoid derivatives LG100268 and LGD1069, which were under development as remedies for promyelocystic leukemia and Kaposi's sarcoma, showed effects in cell culture and animal experiments as follow: (1) these derivatives form heterodimers with PPARγ as an RXR ligand and thus regulate gene transcription; (2) and when orally administered to hereditary obese diabetic mice ob/ob and db/db, they enhance the insulin sensitivity and drastically lower blood glucose levels, serum neutral fat levels and serum insulin levels. The researchers further reported that a significant effect of ameliorating metabolism could be achieved by the combined administration of a retinoid derivative with a TZD compound, each in such a small dose as to show no drug effect alone, and thus indicated that the ligand of RXR and the ligand of PPARγ would exhibit a synergistic effect in vivo.

The retinoid derivatives reported by the researchers were synthesized in order to potentiate the effect of all-trans retinoic acid (ATRA) and alleviate side effects. It is said that these derivatives are effective against skin cancers such as Kaposi's sarcoma and promyelocystic leukemia. Namely, these derivatives also bind to ATRA receptor (RAR) and exert a retinoid activity and, therefore, are poor in specificity of function. In addition, these retinoid derivatives have marked toxicity inherent to ATRA, which makes them unusable as a life-long remedy for diabetes. An RXR-specific ligand, which is free of these problems, has high safety and exerts a considerable effect of potentiating insulin sensitivity, would be a drug showing great promise as a remedy for diabetes and its complications.

It is known that PPARγ receptor is expressed in a large amount not only in adipocyte tissue, which is the target of the treatment for II type diabetes, but also in the spleen, intestinal tract and adrenal gland. Thus, studies are now in progress to determine the roles of PPARγ expressed in these organs. Among them, two noteworthy reports on the role of PPARγ expressed in lymphoid cells have been published recently (M. Ricote et al., The peroxisome proliferator-activated receptor-g is a negative regulator of macrophage activation. Nature 391:79–82, 1998; and C. Jiang, A. T. Tiang and B. Seed. PPARγ agonists inhibit production of monocyte inflammatory cytokines. Nature 391:82–86, 1998). These studies are focused on PPARγ expressed in activated macrophages triggering the induction of chronic inflammation. When macrophages infiltrate an inflammatory site and undergo activation, inflammatory cytokines are synthesized vigorously. However, the transcription of genes relating to such chronic inflammation can be suppressed dose-dependently by adding a nonsteroidal analgesic/anti-inflammatory agent, which is a ligand of PPARγ, to the culture of activated macrophages. It has also been clarified that the ligand of PPARγ competes partially with the transcriptional promotion factors AP-1, STAT and NF-kB, and thus regulates the expression of inflammatory cytokine genes. That is to say, ligands of PPARγ such as nonsteroidal analgesic/anti-inflammatory agents reduce the production of the inflammatory cytokine messenger RNA (IL-1β, TNFα, IL-6, etc.) having been vigorously transcribed in association with the activation of macrophages and, in turn, regulate the production of these inflammatory cytokines. Unfortunately, the existing TZD compounds acting mainly on adipocytes scarcely regulate the production of inflammatory cytokines by activated macrophages. Accordingly, it is impossible at the present stage to treat chronic inflammation with the use of these TZD compounds. However, it has been suggested that regulation of inflammatory cytokines by the ligand of PPARγ may contribute to the treatment of chronic inflammation such as arteriosclerosis, complications of diabetes and rheumatoid arthritis. However, no study has been made so far concerning ligands of RXR which might be capable of forming a heterodimer together with PPARγ, and thereby regulate the expression of a gene signal relating to the onset of chronic inflammation.

It is considered that the function of mechanism of nonsteroidal analgesic/anti-inflammatory agents resides in the suppression of the production of prostaglandins which causes pain and swelling at the inflammation site. However, the authors of the above-described reports suggest that the suppression of the transcription of genes encoding inflammatory cytokines also relate to the function of mechanism as well as the suppression of the biosynthesis of prostaglandins. It is well known that nonsteroidal analgesic/anti-inflammatory agents are effective against rheumatoid arthritis. Sugar corticoids, which are frequently used in treating chronic inflammation similar to nonsteroidal analgesic/anti-inflammatory agents, exert a therapeutic and/or preventive effect on rat adjuvant arthritis which is an experimental model of arteriosclerosis and rheumatoid arthritis. However, these drugs can not be administered over a long time continuously, since they suppress the biosynthesis of prostaglandins in the digestive tract mucosa resulting in a high incidence of digestive ulcers. The suppression of the production of inflammatory cytokines by activated macrophages accumulated at the inflammation site by a ligand of PPARγ not suppressing the prostaglandin biosynthesis, if possible, would, without doubt, make a substantial contribution to the treatment of chronic inflammatory conditions such as arteriosclerosis, complications of diabetes and rheumatoid arthritis. However, at the present stage, such an assumption remains hypothetical, and thus its usefulness needs to be confirmed experimentally and clinically. The TZD compounds, which are synthesized as ligands of PPARγ, exhibit only a weak effect in suppressing the production of inflammatory cytokines, and thus have little practical use. Although TZD strongly acts on PPARγ in white adipose tissue, it shows only a weak effect on activated macrophages. Therefore, it seems that existing TZD compounds are hardly capable of suppressing the production of inflammatory cytokines. Moreover, it is completely unknown what effects ligands of RXR forming a heterodimer with PPARγ exert on activated macrophages. It is also unclear whether or not PPARγ forms a heterodimer with RXR in macrophages, as in adipocyte tissue, and specifically regulates gene transcription. As discussed above, it is known that nonsteroidal analgesic/anti-inflammatory agents serve as ligands of PPARγ and suppress the production of cytokines causative of chronic inflammation at the cell culture level. Thus, the effects of RXR ligands on the production of inflammatory cytokines have also attracted public attention. It is projected that intensive studies will be carried out focusing on ligands of PPARγ and RXR as anti-inflammatory agents against chronic inflammation.

To treat chronic inflammation such as rheumatoid arthritis and autoimmune diseases, it has been a practice to employ nonsteroidal analgesic/anti-inflammatory agents or sugar corticoids which are employed generally in treating acute inflammation. Namely, it can be said that to date there has been no remedy specific for chronic inflammation. Nonsteroidal analgesic/anti-inflammatory agents suffer from a problem that their prolonged use frequently induces has undesirable side effects on the digestive system such as ulcers, since these drugs suppress the biosynthesis of prostaglandins. On the other hand, sugar corticoids have a number of side effects including frequent onset of infectious diseases due to immune suppression, induction of metabolic disorders such as diabetes, and a rebound phenomenon, i.e., whereby discontinuation of administration of the drug brings about a worsening of a treated condition as compared to the state prior to commencement of drug administration. Thus, it can not be said that the quality of life (QOL) of patients is remarkably improved by existing therapies for chronic inflammation. In addition to these problems of drug therapy, attention has to be paid to complications of diabetes occurring due to inflammation in microvessels. Since complications of diabetes fall within the category of chronic inflammation, there is a high possibility that such complications can be prevented and/or treated by administering a drug which exerts an effect of specifically ameliorating chronic inflammation. To treat chronic inflammatory conditions such as rheumatoid arthritis, arteriosclerosis, diabetic microangiopathy, periarteritis nodosa and aneurysm, it is necessary to develop a drug capable of treating chronic inflammation without any worsening of QOL as a result of the frequent occurrence of undesirable side effects.

In postmenopausal females, calcium metabolic disorders arise frequently and osteoporosis is a serious problem in this population group. Osteoporosis is characterized morphologically by a reduction in trabecula, enlargement of Harbor tube, and enlargement of medullary cavity with thinned cortical bone without any morphological change of bone. These pathogenic conditions relate to disorders in the relation between bone resorption and bone addition. Osteopolyporosis observed in postmenopausal females is a typical example. Once suffering from osteoporosis, patients are liable to suffer bone fractures even as a result of slight stresses due to a marked decrease in bone strength. Methods for treating osteoporosis include oral administration of female hormone, activated vitamin $D_3$ or biphosphite drugs and injection of calcitonin. A preferable treatment, for preventing and/or treating osteoporosis would be to potentiate the efficacy of endogenous activated vitamin $D_3$. However, no study has until now been initiated from this viewpoint, due to a lack of possible approaches.

SUMMARY OF THE INVENTION

The present invention has been made based on a novel finding that ascochlorin and its homologues (each having a structure with a terpenoid side chain (preferably carrying about 20 carbon atoms) attached to the 3-position of orcylaldehyde), which have been previously reported by the inventors as fat-soluble antibiotics produced by fungi, are ligands of retinoid X receptor. In particular, the present invention depends on an unexpected finding that, because of having an aldehyde group, ascochlorin and its homologues react with the amino group of serum protein and form Schiff bases in vitro, thereby showing no side effects of retinoids.

Ascochlorin and its homologues are ligands of retinoid X receptor and usable in treating and/or preventing diseases or conditions which can be alleviated by the retinoid X receptor ligand-dependent gene signal transcriptional regulation (for example, diseases caused by the expression of insulin resistance, hypertension, cerebral angiopathy, rheumatoid arthritis, autoimmune diseases, calcium metabolic disorder, complication of diabetes, arterial restenosis following percuneous transluminal coronoary angioplasty, arteriosclerosis following organ transplantation). Also, these compounds inhibit degeneration and/or necrosis of pancreatic Langerhans' islet β-cells and are usable to make these cells to sustain the insulin productivity. Accordingly, the present invention provides pharmaceutical compositions containing these compounds, a therapeutic and/or preventive method with the use of these compounds, and use of these compounds for treating and/or preventing the diseases above.

BRIEF DESCRIPTION OF THE DRAWINGS

FIG. 3 shows arteriosclerosis of the aorta of white rabbits fed with a high fat diet, visible to the naked eye.

DISCLOSURE OF THE INVENTION

Figure 1:
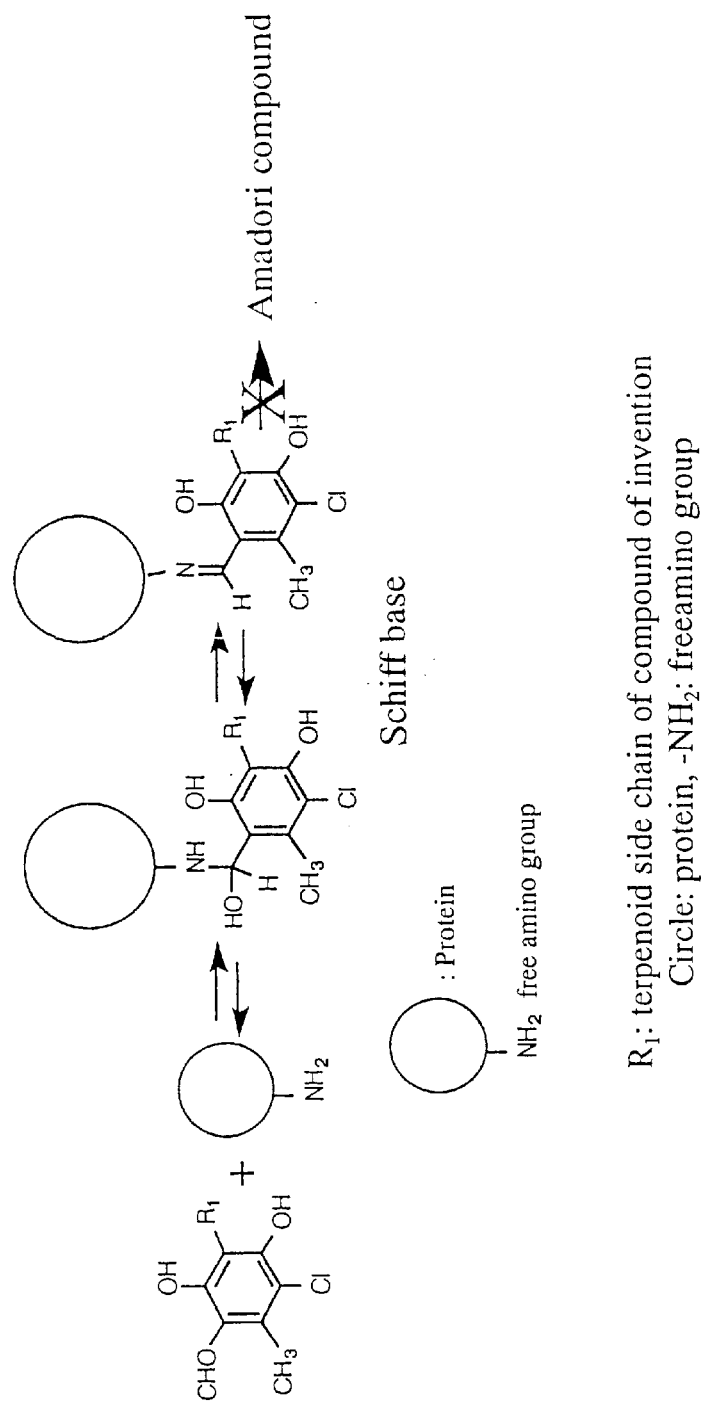
FIG. 1 illustrates a reaction for forming a Schiff base between the compound according to the present invention and serum protein.

The inventors have conducted studies to find an effective means of treating and/or preventing the above-described chronic diseases which cannot be solved by the conventional art and, as a result, completed the present invention.

The present invention relates to ligands of retinoid X receptor selected from among ascochlorin and its homologues. The present invention further relates to retinoid X receptor ligands (RXRLs) selected from the group consisting of ascochlorin and its analogues (namely, cylindrochlorin, 4'-hydroxy-5'-hydroascochlorin, 4'-acetoxy-5'-hydroascochlorin, dihydroascochlorin and chlornectin produced by filamentous fungi), analogues and derivatives thereof wherein the hydrogen of the hydroxyl group(s) at the 2- and/or 4-positions of the orcylaldehyde moiety has been substituted. The present invention furthermore relates to a pharmaceutical composition for treating and/or preventing diseases or conditions which can be alleviated by the retinoid X receptor ligand-dependent regulation of the gene signal transcription, comprising α retinoid X receptor ligand together with a pharmaceutically acceptable additive.

I. Ascochlorin and its Homologues

The term "homologue" as used herein in the expression "ascochlorin and its homologues" means a compound which has a structure similarly to ascochlorin wherein a terpenoid side chain is attached to the 3-position of orcylaldehyde, and which is capable of serving as a ligand of retinoid X receptor. Typical examples of ascochlorin and its homologues (hereinafter sometimes referred to as the compounds of the present invention) include the following compounds:

Formula (1):

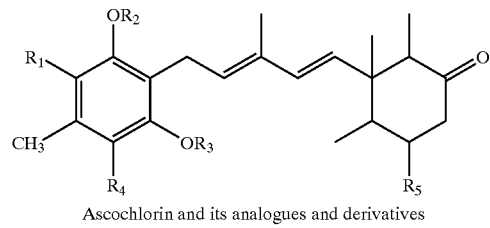

Ascochlorin and its analogues and derivatives

The absolute structure of ascochlorin has been identified as 3-[5-[1(R),2(S),6(S)-trimethyl-3-oxocylohexyl]-3-methyl-2,4-pentadienyl]-2,4-dihydroxy-5-chloro-6-methylbenzaldehyde using X-ray diffractometry by the inventors.

Compounds of Formula (1) include the following ones.

TABLE 1

Ascochlorin and its analogues and derivatives

| # | $R_1$ | $R_2$ | $R_3$ | $R_4$ | $R_5$ | |
|---|---|---|---|---|---|---|
| 1 | —CHO | H | H | Cl | H | Ascochlorin(ASC) |
| 2 | —CHO | H | H | Cl | —OAc | LL-Z1272 ζ |
| 3 | —CHO | H | H | Br | H | bromoASC |
| 4 | —CHO | H | H | H | H | dechloroASC |
| 5 | —CHO | H | $CH_3CO$— | Cl | H | acetylASC |
| 6 | —CHO | H | —$CH_3$ | Cl | H | 4-O-methylASC |
| 7 | —CHO | —$CH_3$ | —$CH_3$ | Cl | H | 2,4-dimethylASC |
| 8 | —CHO | $CH_3CO$— | —$CH_3$ | Cl | H | 4-O-methyl-2-O-acetylASC |
| 9 | —CHO | —$CH_3$ | $CH_3CO$— | Cl | H | 2-O-methyl-4-O-acetylASC |
| 10 | —CHO | —$CH_3$ | H | Cl | H | 2-O-methylASC |
| 11 | —CHO | H | $CH_3CH_2$— | Cl | H | 4-O-ethylASC |
| 12 | —CHO | H | allyl | Cl | H | 4-O-allylASC |
| 13 | —CHO | H | butyl | Cl | H | 4-O-butylASC |
| 14 | —CHO | H | —$CH_2COOH$ | Cl | H | 4-O-carboxymethylASC |
| 15–17 | —CHO | H | —$(CH_2)_nCOOH$ | Cl | H | n = 2~4 |
| 18 | —CHO | H | —$CH_2COOCH_3$ | Cl | H | * |
| 19 | —CHO | H | nicotinoyl | Cl | H | 4-O-nicotinoylASC |
| 20 | —CHO | H | benzoyl | Cl | H | 4-O-benzoylASC |
| 21 | —CHO | H | isonicotinoyl | Cl | H | 4-O-isonicotinoylASC |

Formula (2):

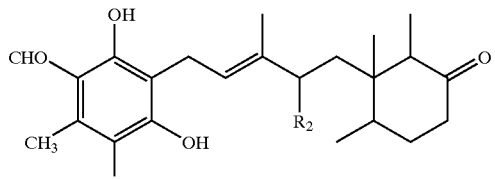

Dihydroascochlorin and its analogues and derivatives

Compounds of Formula (2) include the following ones.

TABLE 2

Dihydroascochlorin and its analogues and derivatives

| # | $R_1$ | $R_2$ | |
|---|---|---|---|
| 22 | Cl | H | dihydroASC |
| 23 | H | H | LL-Z-1272 ε |
| 24 | Cl | —OH | 4'-hydroxy-4',5'-dihydroASC |
| 25 | Cl | —OAc | chlosonectin |

Formula (3):

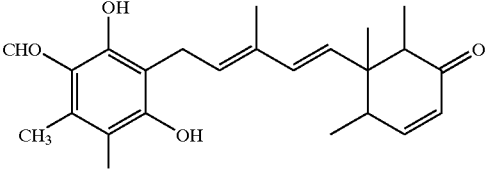

Cylindrochlorin (Compound #26)

Formula (4):

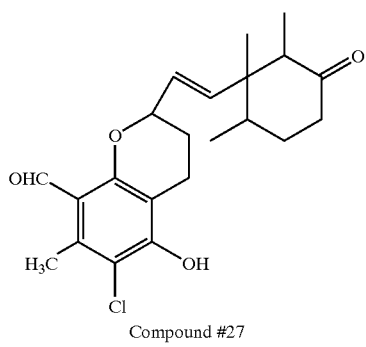

Compound #27

6-Chloro-5-hydroxy-7-methyl-2-[2-(1,2,6-trimethyl-3-oxocyclohexyl)ethenyl-8-chromancarbaldehyde Formula (5):

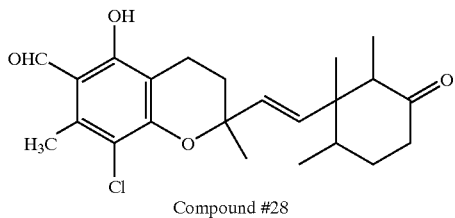

Compound #28

8-Chloro-5-hydroxy-2,7-dimethyl-2-[2-(1,2,6-trimethyl-3-oxocyclohexyl ) ethenyl-6-chromancarbaldehyde Formula (6):

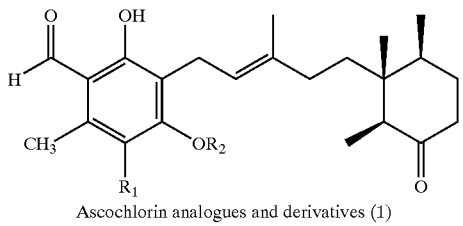

Ascochlorin analogues and derivatives (1)

Compounds of Formula (6) include the following ones.

TABLE 3

| Ascochlorin analogues and derivatives (1) | | |
|---|---|---|
| # | $R_1$ | $R_2$ |
| 29 | Cl | H |
| 30 | Cl | Alkyl group* |
| 31 | Cl | Acyl group** |
| 32 | H | H |
| 33 | H | Alkyl group* |
| 34 | H | Acyl group** |

*Alkyl group: methyl.
**Acyl group: acetyl.

Formula (7):

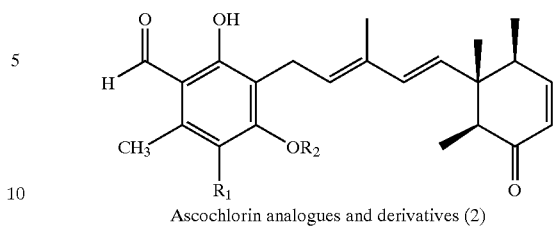

Ascochlorin analogues and derivatives (2)

Compounds of Formula (7) include the following ones.

TABLE 4

| Ascochlorin analogues and derivatives (2) | | |
|---|---|---|
| # | $R_1$ | $R_2$ |
| 35 | Cl | H |
| 36 | Cl | Alkyl group* |
| 37 | Cl | Acyl group** |
| 38 | H | H |
| 39 | H | Alkyl group* |
| 40 | H | Acyl group** |

*Alkyl group: methyl.
**Acyl group: acetyl.

The chemical structures of these compounds are characterized in that a terpenoid side chain is attached to the orcylaldehyde moiety to form a structure analogous to retinoids, as shown below.

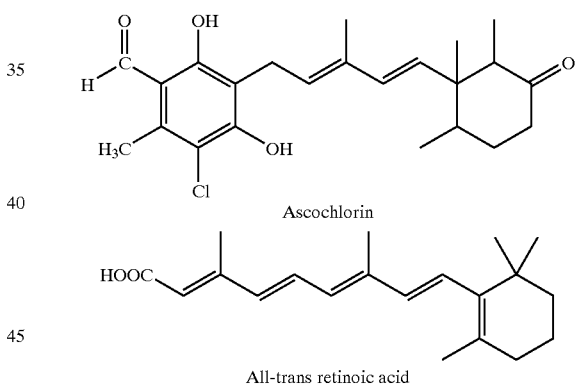

Ascochlorin

All-trans retinoic acid

The compounds of the present invention can be obtained as metabolites produced via fermentation by fungifilamentous or derivatives thereof modified by organic synthesis.

Since the middle of 1960's, the inventors have screened fat-soluble antiviral antibiotics by infecting primary fibroblasts cultures obtained from hatched chick embryos with an animal virus and using the activity of thested compounds to suppress the formation of the thus formed plaques as an indication. During this process, a novel antibiotic named ascochlorin was found as a fat-soluble antibiotic produced by a fungus *Ascochyta viciae* (J. Antibiotics 21:539–544, 1968). The chemical structure of ascochlorin determined by X-ray diffractometry indicated that it compress an orcylaldehyde moiety and an isoprenoid chain having consisting of 15 carbon atoms attached thereto (Bull. Chem. Soc. Japan 44:2652–2660, 1971). It has been reported so far that ascochlorin and its homologues are produced by fungi other than *Ascochyta viciae* too, for example, *Nectria coccinea*, Fusarium sp., *Cylindocarpon lucidium* and Verticillium sp.

Cylindrochlorin, 4'-hydroxy-5'-hydroascochlorin, 4'-acetoxy-5'-hydroascochlorin, dihydroascochlorin, etc. are analogues obtained as by-products in the fermentation of ascochlorin production.

The inventors have further found out that the strong inhibitory effect of ascochlorin on appetite was reduced alleviated in compounds obtained by substituting the hydrogen in the hydroxyl group(s) at the 2- and/or 4-positions of the orcylaldehyde moiety in these compounds. These derivatives correspond to preferred mode for carrying out the present invention. It is preferable that the hydroxyl group(s) at the 2- and/or 4-positions of the orcylaldehyde moiety are alkylated and/or acylated. The term "alkylation" as used herein means substitution of the hydrogen of the hydroxyl group with an alkyl group, unless otherwise noted. The term alkyl group means a linear, cyclic or branched, saturated monovalent hydrocarbyl group. The alkyl group may have any number of carbon atoms, so long as the desired effect by the substitution can be achieved and the inherent function of the compound is not damaged seriously. It is preferable that the alkyl group has from 1 to 10, still preferably from 1 to 5, carbon atoms. The term "acylation" as used herein means substitution of the hydrogen of the hydroxyl group by RCO-, unless otherwise noted. R represents an aliphatic or aromatic hydrocarbyl group. R may have any number of carbon atoms, so long as the desired effect by the substitution can be achieved and the inherent function of the compound is not so seriously damaged. It is preferable that R has from 1 to 20, still preferably from 1 to 10, carbon atoms.

When ascochlorin is reacted with potassium carbonate and an alkyl iodide compound under heating in an organic solvent, for example, the hydroxyl group at the 4-position is first alkylated and then the hydroxyl group at the 2-position is also alkylated in case where the alkyl iodide is present in excess. In the orcylaldehyde moiety of ascochlorin and its homologues, on the other hand, the hydroxyl group at the 4-position alone is selectively acylated while the hydroxyl group at the 2-position forms as intramolecular hydrogen bond with the carbonyl group of the aldehyde and therefore, is not acylated. That is to say, 4-O-acetyl-2-O-alkylascochlorin can be obtained by starting with 4-O-acetylascochlorin and reacting it with an alkyl iodide in the presence of potassium carbonate. By hydrolyzing this product with a caustic alkali, 2-O-alkylascochlorin can be obtained. Compared with ascochlorin, both of 4-O-alkylascochlorin and 2-O-alkylascochlorin show a lower toxicity by oral administration and improved binding selectivity to RXR. Therefore, these derivatives are excellent ligands which are effective even at a low concentration.

II. Function and Effect of the Compounds of the Present Invention

Each of the compounds of the present invention exhibits an activity of binding selectively to retinoid X receptor and regulating the gene signal transcription. Namely, the retinoid X receptors having the compounds of the present invention bonded thereto form dimers with nuclear receptors having respective ligands bonded thereto in cells and then bind hormone response element (HRE) on DNA to thereby regulate the transcription of a specific gene. Moreover, the compounds of the present invention make it possible to easily assay the activity of regulating gene signal transcription by the methods described in Examples hereinafter. Comparison of the ability of the compounds of the present invention to bind RAR with their ability to bind RXR, it is highly characteristic that some of the compounds show higher specificity to RXR than 9-cis retinoic acid (9-CRA) which is a natural RXR ligand. Concerning the expression of luciferase gene serving as a reporter, the compounds of the present invention (i.e., ascochlorin, 4-O-methylascochlorin, 2-O-methylascochlorin, 4-O-acetylascochlorin, etc.) show the peak activity at concentration of from $5 \times 10^{-7}$ M to $1 \times 10^{-5}$ M, though being lower than the peak concentration ($10^{-7}$ M) of 9-CRA. The compounds of the present invention show higher selectivity to RXR than RAR.

TABLE 5

Enhancement in gene signal expression by the compounds of the invention

| Compound | Conc. (M) | Vector RXR | RAR | RXR/RAR |
|---|---|---|---|---|
| All-trans retinoic acid | $10^{-7}$ | 37 | 46 | 0.88 |
| 9-cis Retinoic acid | $10^{-7}$ | 57 | 36 | 1.58 |
| Compound-1 | $10^{-6}$ | 61 | 30 | 2.03 |
| Compound-6 | $5 \times 10^{-6}$ | 55 | 35 | 1.57 |
| Compound-10 | $2 \times 10^{-5}$ | 58 | 40 | 1.45 |
| Compound-14 | $10^{-5}$ | 47 | 38 | 1.23 |
| Compound-26 | $4 \times 10^{-7}$ | 63 | 33 | 1.91 |

Each value means the degree of increase in the luciferase activity, which is expressed by referring the luciferase activity in the control lot as to 1, caused by the addition of the corresponding compound.

Next, illustration will be made how the regulation of gene transcription by the compounds of the present invention relates to pathological conditions. The present invention relates to novel pharmaceutical compositions for treating and/or preventing the peripheral insulin resistance, various chronic inflammations occurring in the heart artery and the brain artery, microangiopathy inherent to complication of diabetes, chronic inflammation in joint and peripheral tissue, calcium metabolic disorder, etc. The compounds of the present invention bind to retinoid X receptor in the target cells, form heterodimers together with other receptors serving as the partner of retinoid X receptor and then bind to the hormone response element on chromosome. When the transcription of gene signal is regulated by binding of these heterodimers, the expression of the gene signal in the target cells, tissue and animal individual varies and thus the expression of the gene participating the pathological onset is suppressed, thereby the pathologic conditions are ameliorated. RXR forms heterodimers together with various nuclear receptors and thus regulates the expression of gene signal. Among all, heterodimers formed by RXR with PPARγ, LXR and VDR are particularly important, since the regulation of the expression of specific gene signals by these heterodimers relates to effects of ameliorating various pathological conditions.

TABLE 6

Effect of nuclear receptor heterodimers comprising RXR as one of the partners

| Heterodimer | Target cell | Affected factor | Medical effect |
|---|---|---|---|
| RXR:PPARγ | Adipocyte | Reduction in release of TNFα. Reduction in release of leptin. | alleviation of insulin resistance. Amelioration of diabetic metabolic disorder. |

TABLE 6-continued

Effect of nuclear receptor heterodimers comprising RXR as one of the partners

| Heterodimer | Target cell | Affected factor | Medical effect |
| --- | --- | --- | --- |
| RXR:PPARγ | Macrophage | Supression of inflammatory cytokine gene transcription. TNFα: reduction in release. IL-1β: reduction in release. IL-6: reduction in release. | Amelioration of chronic inflammation in artery, microvessel, joint, etc. |
| RXR:LXR | Hepatic parenchymal cell | Enhancement of 7-α hydroxylated cholesterol gene transcription → increase the enzyme → increase of bile acid production | Excretion of cholesterol accumulated in liver → decrease in total serum cholesterol. |
| RXR:VDR | Osteoblast and osteoclast | Decrease in serum calcitonin. Decrease in serum PTH. Decrease in serum calcium level. | Normalization of calcium metabolism and amelioration of osteoporosis. |

Now, the novel findings by the inventors will be described. First, PPARγ expressed in adipocytes forms a heterodimer together with RXR and suppresses the production of adipocyte-origin cytokines (mainly THFα) to thereby restore the peripheral insulin sensitivity. This effect depends on dose at the individual animal level too. Even in hereditary obese diabetic mice (db/db mice) which are a type II diabetes model scarcely showing any decrease in the blood glucose level by the administration of insulin, the compounds of the present invention exert the effect of relieving the insulin resistance and thus considerably ameliorating metabolic disorders. After binding to RXR receptor in lymph cells, the compounds of the present invention form heterodimers together with PPARγ receptor binding to a ligand too and thus suppress the production of inflammatory cytokines causing chronic inflammation. As a result, chronic inflammation in vessel, joint and peripheral tissue can be suppressed. On the other hand, a heterodimer formed by LXR and RXR expressed in liver cells enhances the transcription of choleserol-7α hydroxylase gene in the liver and thus accelerates the oxidation of cholesterol into bile acid, thereby promoting the excretion of bile acid. The effect of lowering human serum total cholesterol level exhibited by the compounds of the present invention originates in the function of promoting bile acid excretion. A heterodimer of VDR with RXR in osteoblasts normalizes calcium metabolic disorder and thus ameliorates osteoporosis.

As discussed above, the pharmaceutical compositions according to the present invention aim at treating and/or preventing diseases over a broad range including circulatory diseases (ischemic heart disease, hyperlipoproteinemia characterized by an increase in low-density lipoproteins, hypertension, etc.), metabolic diseases (type I diabetes, type II diabetes, etc.), chronic inflammations (rheumatoid arthritis, etc.), autoimmune diseases and chronic inflammation in artery inducing constriction and obstruction of the inner cavity of various organs (i.e., arteriosclerosis), periarteritis nodosa making artery fragile, topical chronic inflammation (aneurysm, etc.), arterial restenosis following percuneous transluminal coronoary angioplasty, and complication of diabetes ,i.e., chronic inflammation in microvessel (diabetic nephropathy, diabetic neuropathy, diabetic retinopathy, etc.). Moreover, the compounds of the present invention are usable in treating/preventing osteoporosis characterized by calcium metabolic disorder. The compounds of the present invention can be administered to animals including humans in order to treat and/or prevent the diseases as described above.

Next, the process of proving that ascochlorin and its derivatives serve as ligands of RXR and thus exert therapeutic and/or preventive effects on chronic inflammation of many types will be described. Ascochlorin and its derivatives show various biological activities in animal and clinical tests. Since these biological activities seemingly do not relate to each other, the function mechanism forming the basis thereof had been unknown for a long time. The discovery of glucocorticoid nuclear receptor in 1985 and the discovery of RXR receptor in 1990 presented an approach likely leading to the disclosure of the function mechanism of ascochlorin and its derivatives for the first time. PPARγ, which is one of the members of the nuclear receptor superfamily, is expressed in adipocytes and binds to a ligand. Then it forms a heterodimer together with RXR and thus promotes the transcription of a gene promoting the differentiation of precursor cells into adipocytes. It has been clarified that the enhancement of the peripheral insulin sensitivity is caused by the regulation of gene transcription by this heterodimer. From 1982 to 1985, the inventors reported that an ascochlorin derivative Compound-14 enhanced the effect of insulin in hereditary obese diabetic mice and normal mice (T. Hosokawa et al., Agr. Biol. Chem. 34: 2865–2869, 1982; and DIABETES vol. 34:267–274, 1985). Six years thereafter, it was reported that troglitazone, which is a ligand of PPARγ, exerted an insulin-enhancing effect on diabetic animals similar to the compounds of the present invention (T. Fujiwara et al. Diabetes 37:1549–1558, 1988). Based on the effects of these compounds similar to each other, the inventors considered at first that they might have the same function mechanism.

Since ascochlorin and its derivatives exert various effects which cannot be proved as attributable to a ligand of PPARγ, it is obvious that these compounds are not ligands of PPARγ. Thus, the inventors assumed that the compounds of the present invention would likely serve as one of the carriers of heterodimers in the nuclear receptor superfamily and thus form heterodimers together with PPARγ too. From this viewpoint, they have proved that ascochlorin and its derivatives are ligands of RXR through cell culture and animal experiments, thereby completing the present invention. By treating animal cells, which have been transfected with a plasmid wherein an RXR gene vector and a hormone response element are ligated to a reporter gene, with the compounds of the present invention, the transcription of the reporter gene is promoted concentration-dependently as in the case of 9-cis retinoic acid (9-cRA) which is a natural ligand of RXR. Although the compounds of the present invention never induce the differentiation of precursor adipocytes into adipocytes, the differentiation into adipocyte is remarkably promoted by the combined use thereof with a PPARγ ligand at such a low concentration as showing no effect of inducing the differentiation. Thus, it has been also clarified that the ligands of RXR exert a synergistic effect with the ligand of PPARγ. That is to say, it has been clearly found out that the compounds of the present invention form heterodimers together with other members of the nuclear receptor superfamily in vivo and regulate the transcription of a specific gene with the nuclear receptors serving as the partner.

On the other hand, the inventors confirmed in 1970 that the oral administration of ascochlorin to rodents such as mouse and rat exerted an anorexic effect as well as effects of lowering the blood glucose level, the serum lipid level and the serum insulin level. When orally administered to anesthetized rats and hypertensive rats, ascochlorin showed a potent effect of lowering blood pressure. These effects make ascochlorin adequate as a remedy for insulin resistance syndrome. In animal experiments, however, the anorexic effect is similar to the effect of enhancing the action of insulin, which makes it highly difficult to evaluate the drug effect as an insulin enhancing agent. Thus, attempts were made to synthesis derivatives having a relatively weak anorexic effect by synthesizing various derivatives through the modification of the molecular structure of ascochlorin. As a result, it has been found that the anorexic effect can be weakened by substituting the hydrogen atoms attached to the hydroxyl groups at the 4- and/or 2-positions of orcylaldehyde in ascochlorin molecule by various substituents.

When ascochlorin derivatives wherein the hydroxyl group at the 2- or 4-position of the aromatic ring has been substituted by lower alkyl, acyl, carboxymethyl, etc. were administered orally to experimental animals such as normal mice, rats and beagles, these derivatives showed effects of lowering the blood glucose level and the serum total cholesterol level. These derivatives showed an effect of potentiating insulin in normal rodents and pathological diabetic models. For example, Compound-14, which is one of these derivatives, lowered the serum insulin level in normal and diabetic mice, compared with the control group, but lowered the blood glucose level and promoted the discharge of glucose from blood (Hosokawa et al., Agriculture and Biological Chemistry 34:2865–2869, 1982). The compounds of the present invention exert a remarkable effect of ameliorating the metabolism of hereditary obese diabetic mice (db/db mice). Since they lack by heredity a receptor of leptin which is an anorexic protein synthesized and released from adipocyte tissue at satiety, such mice have no appetite control even at satiety. As a result, they suffer from hyperinsulinemia from overeating and peripheral insulin sensitivity is lowered greatly. Therefore, these db/db mice show little decrease in blood glucose level even after the administration of an amount of insulin sufficient to cause hypoglycemic coma in normal animals, and they also show serious obesity, hyperinsulinemia and hyperlipemia. When administered orally to db/db mice, Compound-14 alleviated insulin resistance and significantly lowered blood glucose level, serum lipid level and serum insulin level (T. Hosokawa et al. DIABETES vol. 34:267–274, 1985). A series of studies by the inventors were ahead of ciglitazone which is the oldest TZD corresponding to the forerunner of pioglitazone. In these studies, however, the compounds of the invention were administered within a relatively short time before obesity of db/db mice reached a maximum. Consequently, there is a danger that the results might not express accurately the effects of the compounds of the present invention on long-lasting pathologic conditions in humans.

(Effect of Protecting Pancreatic Langerhans' Islet β-cells)

It has been already supported by the results of several experiments that oral administration of the compounds of the present invention enhances peripheral insulin sensitivity and ameliorates metabolic disorders in db/db mice. It is, however, noteworthy that the compounds of the present invention exert an effect in retaining the function pancreatic synthesis of insulin over a long period, which is defective in diabetes. This effect was clearly indicated by serum insulin level and pathologic observation on pancreas of db/db mice to which Compound-14 had been administered over about 1 year. Compound-14 lowered the blood glucose level of the db/db mice to a level almost comparable to normal litter, suppressed polydipsia and polyuria characteristic to diabetes and drastically reduced urinary glucose to 1/100 or less compared with the control group. Moreover, Compound-14 ameliorated urinary protein throughout the experimental period. In control mice, pancreatic β-cells were exhausted due to the hyperproduction of insulin and insulin productivity was remarkably lowered when body weight attained a maximum (i.e., about 20 weeks after birth). About 40 weeks after birth, these mice suffered form ketosis and had a blood glucose level exceeding 700 mg/dl. Namely, there arose a conversion of non insulin-dependent diabetes mellitus into insulin-dependent diabetes mellitus,analogous to human type II diabetes. Even body weight was reduced to a level similar to that of normal litter after the 40th week, the db/db mice lacking leptin receptor underwent overeating and food energy, which could not be anabolized due to the poverty of insulin, was excreted from the body in a large amount. In this experiment, it is to be emphasized that the function of pancreatic β-cells was completely sustained over 1 year, in spite of the continuous hyperproduction of insulin due to overeating in the group with the administration of Compound-14. Since Compound-6 shows a similar effect, the effect of enabling pancreatic β-cells to sustain their effectiveness in diabetes is one of the major characteristics of the compounds of the present invention.

The effect of the compounds of the present invention in protecting the function of pancreatic Langerhans' islet β-cells was also observed in an experiment wherein aloxan or streptozotocin was administered to rats to rapidly induce insulin-dependent diabetes mellitus. When administered to animals, diabetes-inducing agents such as aloxan and streptozotocin selectively denature pancreatic Langerhans' islet β-cells. It was once considered that this effect would kill pancreatic Langerhans' islet β-cells and, in its turn, cause the termination of insulin production thereby inducing the onset of insulin-dependent diabetes mellitus. By monitoring the process of the onset of insulin-dependent diabetes mellitus caused by diabetes-inducing agents, however, it has been clarified that this process is more complicated. Namely, these diabetes-inducing agents merely trigger the process, and pancreatic Langerhans' islet β-cells which have been denatured by the diabetes-inducing agent and undergone inflammation, are killed as a result of an immunological process which takes 1 to 2 weeks to reach completion following the administration of the diabetes-inducing agent. T lymphocytes, which control cellular immunity, recognize the pancreatic Langerhans' islet β-cells which have been denatured and are suffering from chronic inflammation as foreign matter and attempt to immunologically eliminate and kill these cells, thereby inducing the onset of insulin-dependent diabetes mellitus. Accordingly, the onset of insulin-dependent diabetes mellitus can be prevented by administering cyclosporin, which is capable of inhibiting the function of T lymphocytes, before the completion of the immunological destruction of the pancreatic Langerhans' islet β-cells, even after the administration of a diabetes-inducing agent.

The compounds of the present invention do not have an effect like cyclosporin in suppressing the function of T lymphocytes. When the compounds of the present invention are administered orally before the complete destruction of pancreatic Langerhans' islet β-cells and the onset of insulin-dependent diabetes mellitus, they are capable of interfering with the process of the onset of diabetes, and to alleviate considerably resulting pathological conditions. This effect appears to be derived from the effect of ameliorating chronic inflammation exerted by the compounds of the present invention. That is to say, macrophage cells first recognize the pancreatic Langerhans' islet β-cells, which have been denatured by the diabetes-inducing agent and thus regarded as foreign matter, and present an antigen to lymphocytes which binge? the pancreatic Langerhans' islet β-cells to thereby eliminate these cells. In activated macrophages, the compounds according to the present invention form heterodimers consisting of RXR and PPARγ and thus retard the process of elimination of the denatured pancreatic Langerhans' islet β-cells by lymphocytes thus providing time for repair of the pancreatic Langerhans' islet β-cells. The hereditarily programmed reduction of insulin-producing function observed in hereditary obese diabetic mouse and the disruption of pancreatic Langerhans' islet β-cells rapidly induced by a diabetes-inducing agent have a point in common that the pancreatic Langerhans' islet β-cells undergo immunological self-disruption due to chronic inflammation; though these phenomena differ from each other in rapidity of progression. Therefore, it is reasonable to assume that the compounds of the present invention exhibit a protective effect on pancreatic Langerhans' islet β-cells in two different pathologic models. Pancreatic Langerhans' islet β-cells producing insulin are the main cells implicated in diabetes. The effect of these protecting pancreatic Langerhans' islet β-cells of diabetic animals is a definitive effect of the compounds of the present invention in treating diabetes.

(Similarity in Chemical Structure)

It is of interest that ascochlorin has a chemical structure similar to retinoids. Ascochlorin carries a farnesol side chain which is shorter by one isoprene unit than geranylgeraniol, i.e., a retinoid precursor. The terminal cyclohexanone ring of ascochlorin is structurally similar to the cyclohexene ring of retinoids. As shown by the absolute structure determined by the inventors by X-ray diffractometry, the compounds of the present invention carry, as the side chain attached to 5-position of 2,4-dihydroxy-5-chlorobenzaldehyde, [1'(R),2'(S),6'(S)-trimethyl-3'-oxycyclohexyl-3-methyl-2,4-pentadienyl side chain, 3-methyl-2-pentenyl side chain having reduction in one of the double bonds, 1'(R),2'(S),5'(S)-trimethyl-5'-oxocylohexyl having shift of the carbonyl group of the cyclohexanone ring to the 5-position, or [1'(R), 2'(S),6'(S)-trimethyl-3'-oxocyclohexenyl] group. Furthermore, the carbonyl group of orcylaldehyde counted from the cyclohexyl group is located at the same position as the terminal carboxylate of retinoic acid. These facts indicate that the skeleton of ascochlorin is structurally similar to 9-cis retinoic acid which is an endogenous ligand of RXR. Accordingly, ascochlorin and its derivatives are surely ligands of RXR from the viewpoint of molecular structure too.

The compounds of the present invention significantly suppress arteriosclerosis in white rabbits and Japanese quails fed with a high-cholesterol diet, and inhibit the formation of aneurysm in the mesenteric artery of rats to which mineral corticoid is administered and physiological? saline is given as drinking water. These findings indicate that the compounds of the present invention exert therapeutic and/or preventive effects on chronic inflammation in artery. On the other hand, the effect on adjuvant arthritis of rats indicates that the compounds of the present invention have an effect of ameliorating not only chronic inflammation in artery but chronic inflammation in joint. Moreover, the compounds of the present invention exert a significant therapeutic effect on complication of diabetes which is clinically induced by chronic inflammation in microvessel. The question arises then, as to how the compounds of the present invention can exert the therapeutic and/or preventive effects on these chronic inflammations. In this regard, studies on peroxisome-proliferator activated receptor PPARγ provide a useful indication. It was once considered that PPARγ might be a nuclear receptor which is present in adipocyte tissue, and that it might regulate the expression of gene signal and induce differentiation from precursor cells into adipocytes. At present, it has been clarified that PPARγ is expressed not only in adipocyte tissue but also in intestinal tract, lymph tissue and adrenal gland in a large amount. Also, it has been determined that 15-deoxy-Δ12,14-prostaglandin J2 (15d-PGJ2), which is an endogenous ligand seemingly having the highest affinity with PPARγ, is present not in white adipocyte tissue but in lymph cells such as macrophages.

The production and release of inflammatory cytokines by macrophages, which triggers chronic inflammation, arises in a case where the regulation of the transcription of inflammatory genes by the heterodimer of PPARγ with RXR is malfunctioning. In fact, it has been proved that the compounds of the present invention, which are ligands of RXR, are effective in treating and/or preventing chronic inflammation, dose-dependently, in animal experiments. In clinical tests on subjects with complication of diabetes, these compounds show a therapeutic effect on chronic inflammation too. The discovery of the anti-inflammatory effect of the compounds of the present invention on chronic inflammation corresponds to one.of the main points of the present patent as well as the effects of ameliorating metabolism in diabetes, protecting pancreatic Langerhans' islet β-cells, promoting the synthesis of bile acid in the liver and ameliorating calcium metabolism. In circulatory diseases, chronic inflammation arises in the heart coronary artery, brain artery, etc. In complication of diabetes, it arises in peripheral nerve, kidney, retina, etc. It arises in joint in rheumatoid arthritis and in various peripheral tissues in autoimmune diseases. Moreover, chronic inflammation arises in the artery of a transplanted organ and the coronary artery enlarged with the use of a balloon or a stent. Inhibition of the production of inflammatory cytokines achieved by the compounds of the present invention is the function mechanism common to the suppression of these chronic inflammations occurring in organs and tissues over a wide range.

Among several ten members of the nuclear receptor superfamily, there are several orphan receptors the ligands of which are still unknown. PPARγ forms a heterodimer together with RXR alone, while RXR forms heterodimers together with several nuclear receptors in addition to PPARγ. Therefore, it is one of the focuses in biology today as to how the heterodimers of RXR with receptors other than PPARγ affect biological functions. It is already known that some of these heterodimers such as the heterodimer of RXR with thyroid hormone receptor do not affect the function of thyroid hormone. As disclosed by the present invention, the liver orphan receptor (LXR), which is called cholesterol sensor, and activated vitamin $D_3$ receptor (VDR) form heterodimers with RXR surely affecting gene transcription. It has until now been completely unknown how these heterodimers regulate gene signal expression and affect biological functions. That is to say, the effects of the heterodimers of RXR with LXR or VDR on biological functions have been clarified for the first time by the inventors.

(Clinical Effects)

It is frequently observed that, even though a novel compound having been screened for efficacy on a pathologic model as an indication and proven safe when administered to human subjects, expected effects arise, and thus research and development efforts amount to nothing. However, the efficacy and safety of some of the compounds of the present invention have been confirmed not only by animal experiments but by a phase I clinical test and a phase II clinical test. Namely, the oral administration of compound-6 lowers the serum total cholesterol level and the blood glucose level of patients with type II diabetes and significantly lowers the blood pressure of diabetics with hypertension or borderline hypertension. Because it is capable of significantly ameliorating symptoms relating to diabetic nephropathy and neuropathy, Compound-6 can be said to definitely exert an anti-inflammatory effect in cases of chronic inflammation, which is observed in animal tests, in a clinical setting also. Moreover, Compound-6 ameliorates glucose tolerance in type II diabetes and thus enhances peripheral insulin sensitivity. On the other hand, Compound-6, which is administered in a daily dose ranging from 1 mg/kg to 16 mg/kg, shows no subjective or objective side effect and presents no abnormal data in biological serum examination, blood cell examination, urine examination, etc. Therefore, it may be concluded that Compound-6 has no side effects within the administration range specified above. It is further noteworthy from a clinical viewpoint that the compounds of the present invention exert a remarkable effect on complications of diabetes. Complications of diabetes do not arise in a brief period of time. Namely, the characteristic complication of diabetes induced by microangiopathy in kidney, peripheral nerve and retina would not arise unless one suffers from diabetes for 10 years or longer. Therefore, the therapeutic effect of the compounds of the present invention on complication of diabetes is established not merely by the amelioration of metabolism via the relief of insulin resistance but by the amelioration of chronic inflammation. This therapeutic effect on complications of diabetes is one of the most significant effects of the compounds of the present invention.

(Avoidance of Side Effect Inherent to Retinoids)

There have been accumulated vast data on retinoids which are typical fat-soluble vitamins, and have been studied for a long time. In addition to 9-cis retinoic acid, there have been reported too many derivatives specifically binding to RXR to cite every one of them. Supposing that ligands of RXR have a potential but remarkable effect in treating chronic diseases, a question arises as to why highly effective and safe compounds as drugs have never been isolated from among a number of retinoid derivatives. The answer is that all of the retinoids and their analogues known as ligands of RXR hitherto are strongly toxic to the liver and nervous system. Then, there arises a question why the compounds of the present invention would not show such the toxicity common to retinoids in animals and humans. To answer this question, it is necessary to illustrate differences between retinoids and the compounds of the present invention in absorption, transportation, distribution, metabolism, excretion and the like. When absorbed via the digestive tract, vitamin A, which is a highly fat-soluble substance, binds to serum protein specifically binding to retinoid. When incorporated into target cells, it binds to a protein binding to retinoid in the cells and stored in the liver. Alternatively, it exerts its effect in the target tissue, if necessary. To incorporate the transported vitamin A into target cells, it seems necessary that a retinoid-binding protein in the blood specifically binds to the corresponding receptor on the surface layer of the cells. However, no detailed studies have been made on this point. In any case, retinoid distribution is related closely to specificity. In the case of treating diabetes, retinoids would not be distributed selectively in the target adipocyte tissue or activated macrophages, i.e., the target cells of chronic inflammation. In order to elevate the RXR ligand concentration in the target tissue or target cells to such a level as would enable the regulation of gene signal by administering a retinoid to an animal, the retinoid would need to be administered in excess. When a retinoid is administered in excess, it accumulates in nerve, liver, skin, etc. at a level exceeding the acceptable upper limit and, in its turn, exerts side effects. To sum up, the retinoid derivatives known so far show no distribution specificity to a target organ and thus the occurrence of strong undesirable side effects is unavoidable.

In the case where radioisotope-labeled compounds according to the present invention are administered orally to animals, the compounds are not detected from the plasma though the radioactivity absorbed via the digestive tract appears in portal blood. That is to say, the compounds of the present invention bind strongly to serum protein. Thus, these compounds cannot be released from proteins and recovered into an organic solvent under usual conditions employed for releasing drugs binding to protein. To recover such a compound in a free state from plasma, it is required to add a large amount of a water-miscible organic solvent (methanol, ethanol, acetone, acetonitrile, etc.) to the plasma, acidify the mixture (pH 3.0 or below) and then allow it to stand at room temperature for about 1 week. Even after this treatment, the free compound can be recovered at a yield of about 90% at the highest in terms of radioactivity. Namely, it is impossible to recover 100% of the free compound. Thus, it is assumed that the compounds of the present invention bind to protein not via a protein bond generally observed in a number of drugs but via a covalent bond. The structures of these novel substances derived from the compounds of the present invention and serum protein present in the serum have been clarified by the following experiment. Ascochlorin, Compound-6 or Compound-14 is dissolved in a small amount of an organic solvent and added to serum. Then free compound is continuously decreased in a short half-life. After 24 hours, the free compound is scarcely detected. During this period, the serum turns yellow as the free compound is decreased. This is because the ultraviolet absorption maximum assignable to the aldehyde group inherent to the compound of the invention shifts toward the visible portion due to the addition of the serum. When an organic solvent (ethanol, acetonitrile, etc.) is added to the yellow-colored serum containing the compound of the present invention, the colorant is never dissolved in the solvent, which clearly indicates that the compound tightly binds to protein. It has been determined that this bond is a covalent bond formed by the reaction of the aldehyde group in the compound of the present invention with the amino group of serum protein to form a Schiff base. The Schiff base formed via the bond between the compound of the present invention and serum protein would not undergo Amadori rearrangement, different from the case where a saccharide binds to protein. Therefore, no irreversible advanced glycation end product is formed thereby. Such a Schiff base is completely reversible and hydrolyzed in an organic solvent under acidic conditions to regenerate the compound of the present invention and serum protein. Accordingly, the formation of a Schiff base by the compound of the present invention with serum protein has a buffering effect whereby the biological activity of the free compound absorbed via the digestive tract is transiently masked and the active free compound is gradually supplied to the target tissue.

The Schiff base formed by the reaction of the compound of the present invention with serum protein is an inactivated compound with a masked biological activity. Examination of the distribution of radioactivity in the organs of rats, to which radioisotope-labeled Compound-6 had been administered orally once, indicated that radioactivity rapidly dropped in most of the organs and disappeared after 3 days. This radioactivity was mostly excreted via feces. It is highly interesting that the radioactivity incorporated into white adipocyte tissue (i.e., the target tissue of the treatment of type II diabetes) was elevated day by day. It is still interesting that the radioactive compound incorporated into the adipocyte tissue was free Compound-6 dissolved in oil droplets in cells. It is unknown why the radioactivity is distributed selectively in adipocyte tissue and accumulated with the passage of time. However, this distribution selectivity sufficiently indicates that the compound according to the present invention can ameliorate diabetic metabolic disorder with a high degree of safety. Namely, the compound of the present invention is converted into a highly safe Schiff base with the masked biological activity at the step of being absorbed via digestive tract. This Schiff base is adsorbed on the target cell surface layer and incorporated into the cells via endocytosis. Then it is hydrolyzed to regenerate the free Compound-6. The free Compound-6 is dissolved in oil droplets in depot fat. In adipocytes, it is gradually dissolved in cytoplasm and exerts its effect. When depot fat in white adipocyte tissue is transported into other tissues as an energy source, the free Compound-6 is transported together with the fat. That is to say, it also serves as a depot simultaneously. The compound according to the present invention is hardly incorporated into other tissues. Also, it is neither accumulated nor shows any toxicity unless there are oil droplets of depot fat. Different from retinoids, the compounds of the present invention can exert the effects without causing the side effects inherent to retinoids. The reasons are, without doubt, related to kinetics (absorption, transportation, regeneration of activated compound in target cell surface layer, etc.) of the compounds of the present invention, which differ from those of retinoids. For example, (1) the compounds of the present invention are converted into nontoxic Schiff bases with masked activity in the step of passing through absorptive endothelial cells in intestinal mucosa; (2) different from retinoids, the compounds of the present invention bind to serum protein via covalent bond followed by transportation in vivo; and (3) after being incorporated via the target cell surface layer by endocytosis, Compound-6 is hydrolyzed, regenerated and then dissolved in oil droplets in the cells. FIG. 1 systemically illustrates a reaction for forming a Schiff base between the compound according to the present invention and serum protein.

As discussed above, the compounds of the present invention serve as ligands of RXR receptor (i.e., as a member of the nuclear receptor super family) and thus regulate the expression of gene signal in warm-blooded animals. RXR receptor forms heterodimers not only with PPARγ but also with thyroid hormone receptor (TR), LXR, BXR (an orphan receptor binding to benzoic acid), VDR, etc. so far as known hitherto. It has been further clarified that each heterodimer regulates gene transcription organ- or tissue-specifically and exerts various effects on biological functions. As described herein, it has been clarified in the course of disclosing the function of mechanism of the compounds of the present invention that the RXR ligand-dependent gene signal transcriptional regulation largely affects biological functions over an unexpectedly broad range.

Studies on PPARγ made so far have revealed that tumor necrosis factor (TNFα) released from enlarged adipocytes due to an increase in depot fat lowers the insulin sensitivity in muscle and liver and that a dimer of RXR with PPARγ suppresses the production of THFα to thereby restore the insulin sensitivity. On the other hand, the compounds of the present invention are incorporated into activated macrophages accumulated in chronic inflammation sites induced in arterial wall and joint. Then these compounds serve as RXR ligands to form heterodimers with PPARγ and then bind to a specific site of chromosome, thereby regulating the expression of gene signal concerning inflammation. Thus, these compounds block inflammatory cytokine transcriptional promoter and inhibit the gene signal transcription, thus achieving an anti-inflammatory effect. When incorporated into the liver, the compounds of the present invention form RXR:LXR heterodimers and thus promote the gene transcription in the bile acid biosynthesis pathway. Then, these compounds activate the process of oxidizing cholesterol into bile acid and discharge the excessive cholesterol from the body. RXR forms a heterodimer together with VDR, which is a nuclear receptor of activated vitamin $D_3$, normalizes calcium metabolism in vivo and prevents a decrease in bone mineral density. The compounds of the present invention exert various effects, which seemingly do not relate to each other, in animal experiments and clinical tests. This is because these compounds are ligands of RXR receptor. This is a discovery impacting not only biology but also clinical medicine.

EMBODIMENTS OF THE INVENTION

The compounds of the present invention may be administered by any desired and acceptable administration route for drugs used for similar purposes, either alone or in the form of appropriate preparations. Namely, they may be formulated into solid, semi-solid, freeze-dried powder or liquid preparations (tablets, suppositories, pills, capsules, dusts, solutions, suspensions, emulsions, creams, lotions, aerosols, ointments, gels, etc.) and administered, for example, orally, nasally, parenterally or topically preferably in a suitable single dosage form allowing the administration in an exact dose. These compositions comprise pharmaceutical carriers or excipients commonly employed in the art and the compounds of the present invention optionally together with other drugs for medicinal use, carriers, absorption aids, etc. In general, pharmaceutically acceptable compositions contain from about 1 to 99% (by weight) of the compounds of the present invention and from about 99 to 1% of appropriate medicinal additives depending on the desired administration form. These compositions contain from about 5 to 75% of the compounds of the present invention as a drug for medicinal use and the balance of appropriate fillers for medicinal use. To effectively ameliorate pathologic conditions, the compounds of the present invention are to be administered in a dose of 0.1 to 20 mg/kg/day, preferably 0.2 to 5 mg/kg/day to adults.

To treat the diseases described above in detail, it is preferable to formulate preparations to control the dose depending on the severity of disease. The most important factor in formulating preparations resides in restrictions due to the fact that the compounds of the present invention are soluble in fat and thus restricted in processing. Since ligands of the nuclear receptor superfamily are fat-soluble hormones or vitamins, the compounds of the present invention may be fat-soluble too.

Pharmaceutically acceptable additives for oral administration are prepared by adding arbitrary fillers usable in general, for example, mannitol, glucose, starch, magnesium stearate, saccharin sodium, talc, cellulose, glucose, gelatin, sucrose or magnesium carbonate. These compositions may be in the form of solutions, tablets, pills, capsules, dusts or sustained-release preparations. It is preferable that the compositions are in the form of tablets or pills. These composition may contain, together with the compounds of the present invention, diluents (lactose, sucrose, calcium phosphate, etc.), disintegrating agents (starch, derivatives thereof, etc.), lubricating agents (magnesium stearate, etc.), binders (starch, acacia, polyvinylpyrrolidone, gelatin, cellulose, derivatives thereof, etc.), surfactants moistening the surface of grains of the compounds of the present invention, fat-soluble additives, bile acid, phospholipids and the like. It is particularly preferable that the compositions contain aliphatic synthetic surfactants or polymer auxiliaries soluble in organic solvents. Examples thereof include acacia, sodium alginate, methylcellulose, carboxymethylcellulose, hydroxypropylcellulose, polyvinylpyrrolidone, bentonite, sodium lauryl sulfate, polysorbate 80, sorbitan monofatty acid esters and polyoxyl 40 stearate.

The most important factor in formulating these preparations resides in restrictions due to the fact that the compounds of the present invention are fat-soluble and water-repellent. In general, the absorption of fat-soluble drugs via the digestive tract depends on the speed of the dissolution of individual molecules released from drug grains. Once a fat-soluble drug dissolved in water reaches the absorption site of the digestive mucosa, it is quickly absorbed in practice in a barrier-free state. Even a drug hardly soluble in water can be quickly absorbed by oral administration and achieve a high bioavailability, so long as it can be quickly dissolved in water. It is known that the compounds of the present invention are very slowly dissolved in water. To formulate preparations of these compounds, it is therefore desirable to provide additives which elevate dissolution speed in water and/or to make some treatment in the formulation process. In the case of compounds which are hardly soluble in water and show a very low dissolution speed in water as the compounds of the present invention, one of the treatments for promoting dissolution in water is to minimize drug grain size. That is to say, it is effective (1) to make fine grains of the compounds so as to enlarge the contact area of the grains with water. Even if fine grains of the compounds are formed, dissolution speed in water cannot be elevated if these grains fail to come in contact with water due to the existence of a water-repellent surface, and thus cannot be dispersed in water as fine grains. To bring the grain surface into contact with water, it is therefore preferable (2) to use the compounds of the present invention together with a surfactant or a polymer substance incorporating both fat-soluble and water-soluble groups. It is also useful (3) to accelerate the release of individual molecules from drug grains. In the case where drug grains are crystalline, it is effective to select a crystalline form wherein limited free energy is required to release individual molecules from the crystalline lattice. It is also useful to make the compounds of the present invention amorphous so as to promote the release of individual molecules. Conditions required for the formulation of preparations containing the compounds of the present invention are as claimed in the claims relating to inventions of the compounds of the present invention.

As discussed above, the compounds of the present invention are characterized by: (1) being closely similar in chemical structure to 9-cis retinoic acid which is a natural ligand of retinoid X receptor; (2) promoting the gene transcription at a higher specificity than 9-cis retinoic acid, in a cell culture experimental system to search for ligands of retinoid X receptor activity; (3) when administered to animals including humans, showing an effect of regulating the expression of gene signal by various nuclear receptors forming heterodimers together with RXR; and (4) the aldehyde group reacting with serum protein to form Schiff bases thereby being free from the toxicity inherent in retinoids, though the compounds of the present invention are ligands of RXR inherently having a high toxicity.

Now, the invention will be described in greater detail with reference to the following Examples. However, the scope of the invention should not be construed as being limited thereto.

EXAMPLES

Example 1

For each tablet, 63 mg of cylindrochlorin, 10 mg of sesquioleate sorbitan, 10 mg of powdery silica gel, 40 mg of corn starch, 50 mg of L-hydroxypropylcellulose (PO-30), 12 mg of hydroxypropylcellulose-SL, 46 mg of microcrystalline cellulose, 10 mg of carboxymethylcellulose sodium salt, 3 mg of calcium stearate and 6 mg of talc were mixed together, granulated and tabletted in a conventional manner.

Example 2

To 63 g of ground ascochlorin were added 50 g of lactose, 60 g of corn starch, 30 g of L-hydroxypropylcellulose, 12 g of hydroxypropylcellulose-SL, 46 g of microcrystalline cellulose, 10 g of carboxymethylcellulose sodium salt, 3 g of calcium stearate and 6 g of talc. The obtained mixture was granulated and tabletted in a conventional manner to give tablets each weighing 0.25 g.

Example 3

To 100 g of 4-O-carboxymethylascochlorin (Compound-14) were added 70 g of microcrystalline cellulose, 35 g of lactose, 70 g of carboxymethylcellulose calcium salt, 70 g of corn starch and 5 g of magnesium stearate. The obtained mixture was tabletted in a conventional manner to give tablets each weighing 0.35 g.

Example 4

A plasmid containing a reporter gene regulated in expression by RXR response element and an RXRα expression plasmid were transferred into COS-1 cells. Then these cells were treated with the compounds of the present invention such as ascochlorin. Thus, it was found out that the expression dose of the reporter gene was elevated thereby. The RXR transactivation activities of the compounds of the present invention were lower than 9-CRA but almost comparable to ATRA. These results indicate that the compounds of the present invention are RXR agonists and regulate the gene expression via RXR.

RXR (Retinoid X Receptor) Reporter Gene Transfer

Plasmids were transferred into COS-1 cells. Gene transfer was carried out in a conventional manner with the use of Lipofect AMINE reagent (Life Technologies). $1 \times 10^5$ cells were dispersed in 2 ml of Dulbecco's modified Eagle medium (DMEM) containing 10% of fetal calf serum and poured into a 35 mm Petri dish. After culturing in a $CO_2$ incubator for 17 hours, the medium was removed and the cells adhering to the Petri dish were washed with phosphate-buffered saline (PBS). Then gene transfer was carried out by using Lipofect AMINE reagent. Namely, 500 ml of a minimum serum medium OptiMEM (Life Technologies) containing 4 mg of a plasmid containing a luciferase gene under the regulation in expression by RXR response element (PRXRL: RXRE-SV40 luciferase; a reporter gene plasmid wherein RXRE has been ligated to SV40 promoter and luciferase cDNA, under the regulation in expression thereby, has been located downstream thereof); 4 mg of an RXRα expression plasmid (pRXRα; a plasmid wherein human RXRα CDNA has been ligated to the downstream of a cytomegalovirus promoter to express human RXRα in mammalian cells); and 2 mg of a β-galactosidase gene plasmid to assess the gene transfer ratio (pCH110; Pharmacia) were pre-mixed with 500 ml of OptiMEM containing 50 ml of Lipofec AMINE, and the resultant mixture was maintained at room temperature for 15 minutes. 100 ml of this liquid mixture was mixed with 400 ml of OptiMEM, and the medium mixture was divided to the Petri dish. After maintaining in a $CO_2$ incubator at 37° C. for 3 hours, the gene transfer medium was sucked off from the Petri dish and DMEM medium containing a test substance and 10% of serum (activated carbon-treated) was added thereto followed by culturing at 37° C. for 20 hours. As the test substances, Compounds-1, -5, -6, -7, -10, -14, -19, -26 and -28 (each at $10^{-8}$, $10^{-7}$ and $10^{-6}$ M) were used while all-trans retinoic acid, 9-cis retinoic acid and dexamethasone were used as a control. Further, dimethyl sulfoxide (final concentration: 0.1%) was added as the solvent for the test substance.

RAR or GR (Glucocorticoid) Reporter Gene Transfer

As a substitute for a plasmid containing a luciferase gene under the regulation in expression by RXR response element (pRXRL:RXRE-SV40 luciferase), and the RXRα expression plasmid (pRXRα); a plasmid containing a luciferase gene under the regulation in expression by RXR response element (pRARL:RASE-SV40 luciferase), and a GR expression plasmid (pRARα) were transferred into COS-1 cells. Transfectants with these plasmids and the compound of the present invention (concentration: $10^{-4}$ to $10^{-7}$ M) were added to the culture. As control compounds, all-trans retinoic acid ($10^{-8}$, $10^{-7}$ and $10^{-6}$ M), 9-cis retinoic acid ($10^{-8}$, $10^{-7}$ and $10^{-6}$ M), dexamethasone ($10^{-8}$, $10^{-7}$ and $10^{-6}$ M), etc. were added.

After sucking off the medium from the Petri dish, 250 ml of a cultured cell lysing solution (25 mM Tris phosphate buffer (pH 7.8), 2 mM 1,2-diaminocyclohexane-N, N,N',N'-tetraacetate, 10% glycerol, 1% Triton X-100) was added and the cells were peeled off with a rubber policeman and collected. After completely disrupting the cells by freezing and melting, the cells were centrifuged at 4° C. (15,000 rpm, 2 min) and the supernatant thus obtained was employed as a sample for measurement. To 20 ml of the supernatant, 100 ml of a luciferase substrate solution (2.14 mg of Co-A, 100 ml of 470 mM D-Luciferin, 200 ml of 530 mM ATP, 2 ml of DTT-Tricine buffer (pH 7.8)) was added and the fluorescence intensity was measured with a luminometer (ATTO Luminosensor AB-2000). To measure the β-galactosidase for determining the gene transfer efficiency, using a Luminescent β-galactosidase detection kit II (Clontech), fluorescence intensity was measured by a luminometer. As already shown by Table 2, it was thus found out that the compounds of the present invention are ligands specific to RXR though their activities are somewhat lower than 9-cis retinoic acid. Although these compounds showed activities for RAR corresponding to about 25 to 40% of those for RXR, they did not activate GR at all. Thus, it is clearly indicated that the compounds of the present invention are ligands specific to RXR.

Example 5

Pancreas Function Protecting Effect on Hereditary Obese Diabetic Mice

Figure 2:
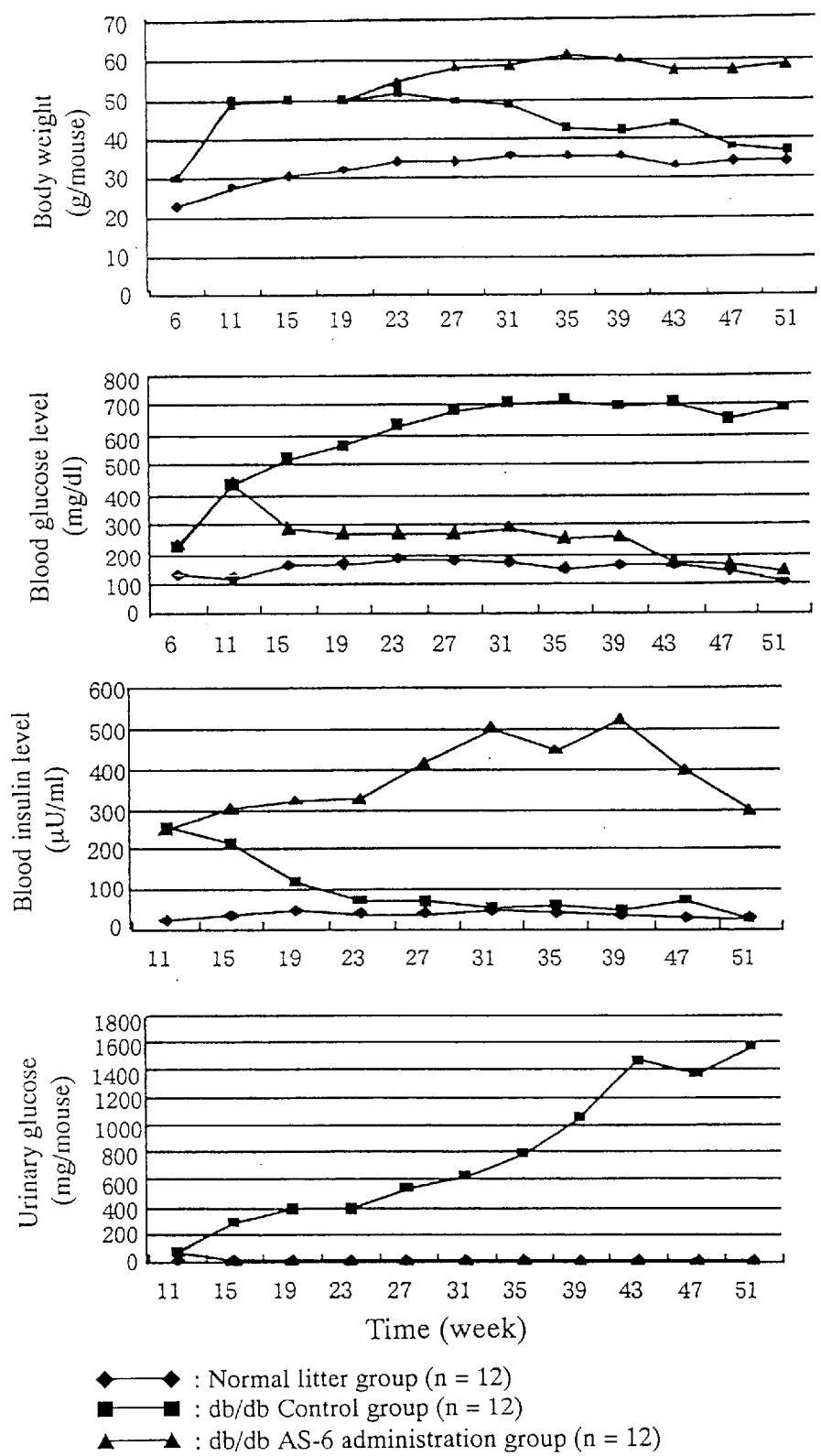
FIG. 2 shows body weight, blood glucose level, blood insulin level and urinary glucose of hereditary obese diabetic mice C57BL/ksj db/db which orally received Compound 14 for 40 weeks.

Since they lack hereditarily leptin reporter, db/db mice have no appetite control even at satiety. As a result, they suffer from hyperinsulinemia due to overeating and serious obesity, thereby undergoing the onset of diabetes. The compounds of the present invention were orally administered to db/db mice for 40 weeks (from 11 to 51 weeks after birth) (FIG. 2).

During the period where the mice underwent serious obesity (until the 20th week after birth), insulin resistance of peripheral tissue was gradually enhanced and thus the blood insulin level was gradually elevated. As obesity attained a maximum, insulin requirements exceeded insulin production levels. Thus, pancreatic Langerhans' islet β-cells having insulin depot granules therein were mostly degranulated and there arose insulin depot poverty. The pancreatic Langerhans' islet β-cells having been working severely to produce insulin in excess gradually fatigued. From the point at which obesity attained the maximum level, degeneration and/or necrosis of the pancreatic Langerhans' islet β-cells became susceptible and, at the same time, blood insulin level was quickly lowered. From 23rd week after birth, it became impossible to anabolize all of the food energy taken in excess due to the insufficient function of insulin, which induced a decrease in body weight. The food energy which could not be anabolized was excreted as urinary glucose. As a result, the urinary glucose increased with a decrease in the blood insulin level. About 50 weeks after birth, the hereditary obese diabetic mice showed body weight reduced to a level comparable to normal litter (i.e., ½ to ⅓ of the maximum body weight) and a remarkably high level of the blood glucose over 700 mg/dl, and excreted a large amount of glucose into urine. At this point, the blood insulin level was lowered to a level almost comparable to normal litter. Namely, there arose the conversion of noninsulin-dependent diabetes mellitus into insulin-dependent diabetes mellitus in clinical case of humans. In the case of db/db mice fed with a feed containing 0.1% of Compound-14, glucose was scarcely excreted into urine from immediately after the initiation of the administration and the blood glucose level was gradually lowered toward the normal level. About 40 weeks after birth, the db/db mice showed a blood glucose level almost comparable to normal litter. However, Compound-14 has no function of restoring leptin receptor and thus exerts no effect on the process of the induction of obesity by hyperinsulinemia due to overeating.

Concerning the effects of Compound 14, it is important to note that its administration does not give rise to any significant decrease in insulin production due to the fatigue of pancreatic Langerhans' islet β-cells, although the administration of the compound compels pancreatic Langerhans' islet β-cells to function to a point of f hyperinsulinemiathe, in addition to normalizing blood glucose level and remarkably reduce urinary glucose. Since pancreatic Langerhans' islet β-cells are of key importance in various aspects of diabetes, the ability of the compound of the present invention to maintain the function of these cells over a long period of time, is very important in terms of the treatment and prevention of diabetes.

Example 6

Eighteen male Wistar rats weighing about 200 g were divided into 3 groups at random. To the animals of 2 groups, 45 mg/kg of streptozotocin was intravenously administered. One of these groups was regarded as a control group, while the other was regarded as the Compound-6 administration group. To the remaining 1 group which was regarded as the normal control group, a 1/10 M citrate buffer (pH 3.5) containing streptozotocin dissolved therein was intravenously administered. Immediately after the administration of streptozotocin, a suspension of Compound-6 in acacia was orally administered once a day continuously for 10 days in a dose of 20 mg/kg/day. To other groups, an acacia solution alone was administered. After fasting for 6 hours after the final administration, blood was collected from the heart of each animal and the blood glucose level and the blood insulin level were measured. As the data given in Table 7a show, the oral administration of Compound-6 inhibited an increase in the blood glucose level and a decrease in the blood insulin level.

Eighteen male SD rats weighing about 250 g were divided into 3 groups at random. One of these groups was regarded as the normal control group, while the remaining 2 groups were regarded to as the streptozotocin administration groups. From 24 hours after the intravenous administration of 50 mg/kg of streptozotocin, 10 mg/kg/day of Compound-5 suspended in an acacia solution was orally administered once a day (early morning) for 14 days continuously. To the normal control group and the streptozotocin control group, the acacia solution alone was administered orally. After fasting for 6 hours after the final administration, blood was collected from the heart of each animal and the blood glucose level and the blood insulin level were measured. As the data given in Table 7b show, the oral administration of Compound-5 inhibited an increase in the blood glucose level and a decrease in the blood insulin level.

TABLE 7

Relief of onset of streptozotocin-induced diabetes by compounds of invention

| | Dose (mg/kg) | Blood glucose (mg/dl) | Serum IRI (mU/ml) |
|---|---|---|---|
| a. Relief of onset by Compound-6 (Mean ± SE) | | | |
| Normal group (control) | — | 159.7 ± 3.89 | 21.7 ± 2.87 |
| Diabetic group (control) | — | 672.1 ± 40.76 | 2.7 ± 0.88 |
| Diabetic group (treated) | 20 | 277.2 ± 52.44* | 12.3 ± 1.65* |
| b. Relief of onset by Compound-5 (Mean ± SE) | | | |
| Normal group (control) | — | 120.5 ± 3.50 | 25.2 ± 2.99 |
| Diabetic group (control) | — | 667.8 ± 53.71 | 2.1 ± 1.12 |
| Diabetic group (treated) | 10 | 237.2 ± 26.31* | 15.5 ± 2.16* |

*$P < 0.05$ (significant difference from diabetic control group).

Example 7

Effect of Inhibiting Arteriosclerosis in White Rabbits

It is known that white rabbits suffer from arteriosclerosis and undergo circulation disorder within a relatively short period of time when fed with a fat-enriched diet. Thus, a high fat feed was prepared by adding 10% of hardened coconut oil, 2% of cholesterol, 0.5% of bovine bile powder and 0.04% or 0.01% of ascochlorin to a powdery marketed standard white rabbit feed and molded the mixture into pellets. Separately, another high fat feed for the control group was prepared without using ascochlorin. Moreover, 0.2% of clofibrate (i.e., a PPARα ligand) was added as a control drug to the feed to give another high fat feed.

Twenty-four white rabbits weighing about 2 kg were divided into 4 groups at random. One of these groups was regarded as the control group, while the remaining 3 groups were respectively regarded as the clofibrate group, the ascochlorin 0.01% group and the ascochlorin 0.04% group at random. Then the experiment was carried out for 14 weeks. FIG. 3 shows the results. From about the 6th week of the experiment, the animals of the control and clofibrate groups lost appetite 2 animals among six of each group died from circulatory insufficiency due to obstruction in the coronary artery in the course of the experiment. In the animals of the ascochlorin 0.01% and ascochlorin 0.04% groups, in contrast thereto, the lesions of obstruction in the coronary artery were significantly alleviated and all individuals survived until the completion of the experiment. It is to be emphasized that ascochlorin and clofibrate would not suppress increase in the serum total cholesterol level. The serum total cholesterol level of the white rabbits (about 50 mg/dl immediately before the initiation of the experiment) showed a rapid increase in each group and exceeded 1 g/dl after 1 month. Thus, the plasma became cloudy just like cow's milk. The serum total cholesterol levels of all groups were almost the same, which indicate that low-density lipoprotein was incorporated into the arterial wall at almost the same ratio in these groups. Inhibition of arteriosclerosis by ascochlorin strongly suggests that the process from the infiltration of leukocytes into damaged artery to arteriosclerosis via chronic inflammation was inhibited thereby.

Example 8

Effect of Inhibiting Arteriosclerosis in Japanese Quails

When fed with a high fat diet, birds also show the onset of arteriosclerosis within a short period of time. Then 32 adult Japanese quails aged about 30 days were divided into 4 groups at random. One of these groups was regarded as the standard feed group, another one was regarded as the high fat feed control group and the remaining 2 groups were regarded respectively as the high-dose Compound-6 group and the low-dose Compound-6 group each with a high fat feed. The feed was prepared by adding 1% of cholesterol to a powdery protein-rich standard fed for chick and molding the mixture into pellets. Compound-6 was added in an amount of 0.16% or 0.0025% to the powdery feed and then the mixture was molded into pellets. The experiment was carried out for 9 months. During this period, the birds were allowed to take the feed and drinking water ad libitum. The feed employed in this experiment contained less fat, compared with the feed employed in the experiments with white rabbits, and was free from bile acid promoting the absorption of cholesterol from the digestive tract. As a result, no Japanese quail suffered from serious circulatory disorder and the feed intake showed no difference among groups throughout the experiment.

After 9 months, blood was collected and the serum total cholesterol level and the neutral fat level were measured. Compared with the control group fed with the standard feed, the control group fed with the high cholesterol feed showed serum total cholesterol level higher by 13 times and serum neutral fat level higher by 4 times. The cholesterol and neutral fat levels were decreased each by 40% in the high-dose Compound-6 group, and respectively by 25.5% and 21.6% in the low-dose Compound-6 group. Each bird was dissected and the aorta was taken out. Then the severity was scored in 5 grades based on the ratio of atheroma to the total endosporium area and thickening of the arterial wall. As a result, the high cholesterol feed group showed atheroma lesions in ⅞ and the atheroma severity was 2.21 on average. In contrast, the high-dose Compound-6 group showed no atheroma, while the low-dose Compound-6 group showed atheroma in ½ of the birds and a considerably alleviated severity score of 0.50.

These experimental data indicate that not only the mother compound ascochlorin but also its derivative with the modification of the hydroxyl group at the 4-position has an effect of inhibiting arteriosclerosis and that the effect of inhibiting arteriosclerosis is further potentiated in parallel to the suppression of increase in the serum low-density lipoprotein level as in this experiment.

TABLE 8

Serum lipid level of Japanese quails fed for 9 months with standard feed for chick containing Compound-6 and 1% of cholesterol

| Group | Cpd.-6 (%) | Serum total cholesterol (mg/dl) | Serum neutral fat (mg/dl) |
|---|---|---|---|
| Control | 0 | 2013 ± 193 | 654.6 ± 64.0 |
| Low-dose | 0.0025 | 1499 ± 120* −25.5% | 513.1 ± 39.2 −21.6% |
| High-dose | 0.16 | 1200 ± 136** −40.4% | 392.6 ± 46.5* −40.0% |

(Mean ± SE) *P < 0.05 and **P < 0.01, in Student t-test

TABLE 9

Atheroma formation in arcuate aorta of Japanese quails fed for 9 months with standard feed for chicken containing 1% of cholesterol

| Individual No. | Control group | Low-dose group | High-dose group |
|---|---|---|---|
| I | II | 0 | 0 |
| II | I | 0 | 0 |
| III | IV | 0 | 0 |
| IV | 0 | I | 0 |
| V | I | 0 | 0 |
| VI | II | I | 0 |
| VII | III | I | 0 |
| VIII | IV | I | 0 |
| Average | 2.12 ± 0.52 | 0.50 ± 0.199** | 0.00 ± 0.00** |

Onset of atheroma in arcuate aorta:

- 0: no atheroma.
- I: coated with atheroma at a ratio of 1 to 10% of the total area.
- II: coated with atheroma at a ratio of 11 to 40% of the total area.
- III: coated with atheroma at a ratio of 41 to 70% of the total area.
- IV: coated with atheroma at a ratio of 71 to 100% of the total area.

Example 9

Effect of Inhibiting Aneurysm

The compounds of the present invention show an effect of inhibiting periarteritis nodosa in a malignant hypertension model rat in which periarteritis nodosa arises in the mesenteric artery and progresses into aneurysm. Among aneurysms, those formed in the mesenteric artery can be treated quantitatively. Thus, the mesenteric artery was taken out and fixed with formalin. Then it was fat-stained and arterioles and aneurysms were counted thrice and the average aneurysm count per arteriole was calculated. To rats with renal hypofunction due to the excision of one kidney, 0.9% saline, having a somewhat higher osmotic pressure than plasma, was given as drinking water and 10 mg/kg of deoxycorticosterone acetate (DOCA) (a mineral corticoid) was subcutaneously administered at intervals of 1 week. Twenty-four male Wistar rats were divided into 4 groups at random. After taking out the left kidney, each animal was allowed to stand and the operative wound was fused. One week thereafter, one of these groups was regarded as the control group while 10 mg/kg/day and 40 mg/kg/day of Compound-6 was administered to two of the remaining groups continuously. The experiment was carried out for 7 weeks. Since the initiation of the experiment, the feed intake, water intake, urine, body weight and blood pressure of each group were measured once every three days.

The control group showed a rapid increase in blood pressure. The average blood pressure exceeded 180 mmHg in the 3rd week and attained 200 mmHg in the 4th week. Compared with the control group, the groups with the administration of the compound of the present invention showed a significant effect of inhibiting increase in blood pressure in the 2nd and 3rd weeks, though no significant difference was observed thereafter. The administration groups showed significant effects of decreasing water intake, decreasing urine, sustaining the ability to concentrate urinary electrolyte, ameliorating body weight gain speed, etc. In the 7th week, each animal was dissected and the mesenteric artery was taken out. After treating with formalin, the artery was fat-stained and aneurysms were counted. No individual of the normal control group showed aneurysm. On the other hand, all of the individuals in the hypertension control group showed aneurysms and the average aneurysm count per mesenteric artery was 1.67±0.68, thereby indicating that hypertensive arterial lesions had been in progress. The low-dose Compound-6 group showed 0.66±0.41 aneurysms per arteriole on average. In the high-dose Compound-6 group, the average aneurysm count per arteriole was lowered to 0.27±0.05.

Namely, it has been clarified that the compound according to the present invention strongly suppresses the onset of aneurysm induced by vascular lesion at a branched site mainly caused by hypertension.

TABLE 10

Effect of Compound-6 of inhibiting aneurysm formation in the mesenteric artery of DOCA hypertensive rats

| Group | Rat no. | Arteriole count | Node count | Appearance frequency[a] (%) | Lesion index[b] |
|---|---|---|---|---|---|
| Control | 19 | 11.00 | 35.67 | 324.27 | 4 |
|  | 20 | 14.67 | 8.00 | 54.53 | 2 |
|  | 21 | 15.33 | 8.67 | 56.56 | 2 |
|  | 22 | 9.33 | 39.33 | 421.54 | 4 |
|  | 23 | 15.00 | 2.00 | 13.33 | 1 |
|  | 24 | 15.67 | 20.67 | 131.91 | 3 |
|  | Avg | 13.50 | 19.06 | 167.02 ± 68.12 | 2.67 ± 0.49 |
| 10 mg/kg | 25 | 9.00 | 2.33 | 25.89 | 1 |
|  | 26 | 11.33 | 2.33 | 20.56 | 1 |
|  | 27 | 11.00 | 3.00 | 27.27 | 1 |
|  | 28 | 14.67 | 40.33 | 274.91 | 4 |
|  | 29 | 17.00 | 5.67 | 33.35 | 1 |
|  | 30 | 13.33 | 2.00 | 15.00 | 1 |
|  | Avg | 12.72 | 9.27 | 66.16 ± 41.83 | 1.50 ± 0.50 |
| 40 mg/kg | 31 | 12.67 | 1.00 | 7.89 | 1 |
|  | 32 | 10.33 | 0.33 | 3.19 | 1 |
|  | 33 | 12.00 | 2.00 | 16.67 | 1 |
|  | 34 | 13.67 | 5.00 | 36.59 | 1 |
|  | 35 | 13.00 | 3.33 | 25.62 | 1 |
|  | 36 | 15.00 | 4.33 | 28.87 | 1 |
|  | Avg | 12.78 | 2.67 | 26.57 ± 5.24*** | 1.00 ± 0.00*** |

Arterioles and nodes in the mesenteric artery were each counted thrice and the average was calculated.

a) Appearance frequency=node count/arteriole count×100 (%).
b) Lesion index: evaluated as follows:
   0: node count in the mesenteric artery; 0.
   I: node count; 1 to 50%.
   II: node count; 51 to 100%.
   III: node count; 101 to 200%.
   IV: node count; more than 201%.

Example 10

Therapeutic Effect on Rat Adjuvant Arthritis

To discuss whether or not the compounds of the present invention are effective against not only chronic inflammation in artery but general chronic inflammation, the effect on rat adjuvant arthritis, which is a typical chronic inflammation mode, was examined.

Rats with arthritis employed in Experiment 1 were individuals which suffered from serious arthritis caused by the injection of an adjuvant 45 days ago and thus crawled on forelegs since they could not bend hind legs. Drug effects were evaluated by observing walking, observation with the naked eye of the severity of inflammation in hind legs and the volume of swelling in legs. To 19 SD male rats (weighing about 300 g), Freund's incomplete adjuvant containing dead tubercle bacillus Aoyama B strain was subcutaneously injected into the tail root to induce arthritis in hind legs. Compound-6 was suspended in a tragacanth gum solution and orally administered at a ratio of 0.5 ml/100 g body weight. Compound-6 was administered to 3 groups including the high-dose model (HM; 50 mg/kg), the medium-dose model (MM; 25 mg/kg) and the low-dose model (LM; 10 mg/kg). Administration was made once a day in morning continuously 7 times. During this period, the hind leg volume was measured at the initiation of the experiment and 2, 4 and 7 days thereafter. The volume change was calculated by referring the volume at the initiation of the experiment as to 100%. On the 7th day, the inflammation conditions in hind legs were evaluated in 5 grades with the naked eye.

After 1 week, the control group showed no large difference in the severity of inflammation and the leg volume from immediately before the initiation of the experiment. However, it was surprising that all of the rats of the Compound-6 groups, which had been disabled to the point of being unable to bend their hind legs due to swelling in joint, could walk again owing to the effect of Compound-6. As a matter of course, the volume of swelling in legs was largely reduced too. Ascochlorin and its derivatives such as Compound-14 showed similar effects. Based on these results, it has been proved that the compounds of the present invention exert an effect of ameliorating not only arterial inflammation but chronic inflammation in joint. Immediately after administration, the three Compound-6 groups were combined and divided again depending on the occurrence of arthritis (i.e., positive and negative groups). Then the data were compared with the data of the control group. All of the individuals in the control group suffered from arthritis. When appearance frequency was calibrated between the Compound-6 group and the control group, a significant difference was observed at a hazard rate of 5%. This fact indicates that Compound-6 is obviously effective in treating sever arthritis.

TABLE 11

Body weight gain and inflammation in hind legs of each group on the day 7

| | Body weight change (g/rat)* | Inflammation score** |
|---|---|---|
| Control (n = 5) | 2.9 | 4.4 |
| HM group (n = 5) | 2.2 | 2.2 |
| MM group (n = 5) | 3.9 | 2.8 |
| LM group (n = 5) | 2.0 | 3.2 |

*: (Body weight immediately before the initiation of administration) − (body weight immediately after the completion of administration).
**: Inflammation scores: inflammation severity in hind legs was evaluated as follows;
5: disable to normally walk due to swelling in both hind legs.
4: disable to normally walk due to swelling in one hind leg.
3: able to walk in spite of swelling in both hind legs.
2: able to walk in spite of swelling in one hind leg.
1: normal in both hind legs.

| Chi-square test | | | |
|---|---|---|---|
| | Arthritis (−) | Arthritis (+) | Total |
| MAC group | 7 | 7 | 14 |
| Control group | 0 | 5 | 5 |
| Total | 7 | 12 | 19 |

Theoretical value at 5% of significant difference corresponding to degree of freedom of 1=3.84. Calibrated value=3.96. Thus, $P<0.05$.

Example 11

Effect of Lowering Serum Total Cholesterol Level in Mice

Effect of serum cholesterol lowering agents varies among animals. Namely, some agents which are effective on a certain animal exert any effect on others. For example, compactin, which is an HMG CoA reductase inhibitor, cannot lower the serum total cholesterol level when administered to rodents such as rat or mouse. This is because even though HMG CoA reductase is inhibited in the rodent liver, the enzyme is biosynthesized in an amount in excess of that for compensating the inhibition so that the inhibitory effect is negated. Accordingly, it is favorable to calibrate the effect of lowering serum total cholesterol level in as many animals as possible. Concerning the effect of the compounds of the present invention on the serum total cholesterol level, an assay was made with the use of mice. After adding these compounds to a standard powdery feed for rat and mouse, the resultant mixtures were molded into pellets and given for 8 days to male ICR and ddY mice aged 5 weeks. In the afternoon of the day 8, the blood of each animal was collected from the heart and the total cholesterol in the serum was determined. The doses were determined as the maximum dose, in which body weight gain was not suppressed after orally administering for 1 week, and as the ¼ dose thereof. Table 12 shows the result:

TABLE 12

Serum total - lowering effect of compounds of invention in mice

| Cpd. no. | Test group | cholesterol mg/dl | % change | Cpd. no. | Test group | cholesterol mg/dl | % change |
|---|---|---|---|---|---|---|---|
| 1[a] | Control | 155 ± 3.0 | | 14 | Control | 117 ± 3.0 | |
| | 0.04% | 131 ± 6.7** | −15 | | 0.04% | 100 ± 4.4** | −14 |
| | 0.01% | 138 ± 5.1** | −11 | | 0.01% | 109 ± 2.8 | −7 |
| 5 | Control | 160 ± 3.7 | | 19 | Control | 105.2 ± 3.4 | |
| | 0.04% | 117 ± 3.3** | −27 | | 0.04% | 88 ± 3.0** | −16 |
| | 0.01% | 132 ± 6.1* | −13 | | 0.01% | 91 ± 4.5** | −13 |
| 6 | Control | 110.4 ± 6.5 | | 26 | Control | 146 ± 4.8 | |
| | 0.04% | 92 ± 3.3* | −17 | | 0.04% | 110 ± 5.4** | −24 |
| | 0.01% | 93 ± 4.4 | −16 | | 0.01% | 132 ± 6.1* | −10 |
| 7 | Control | 174 ± 11.2 | | 6 | Control | 118 ± 4.9 | |
| | 0.04% | 120 ± 5.9** | −31 | | 0.04% | 75 ± 4.4** | −38 |
| | | | | | 0.01% | 103 ± 1.2** | −13 |
| 10 | Control | 186 ± 6.4 | | 14 | Control | 201 ± 11.1 | |
| | 0.04% | 122 ± 3.0** | −34 | | 0.04% | 144 ± 7.2** | −28 |
| | 0.01% | 130 ± 4.5* | −30 | | 0.01% | 174 ± 4.9* | −13 |

Each value is represented in Mean±SE (n=10). a) In the case of Compound-1, the control group consisted of 23 animals while the 0.04% and 0.01% groups each consisted of 12 animals.

Example 12

Promotion of Bile Acid Excretion and Promotion of Cholesterol-7α Hydroxylase Transcription in Rats Feed-origin cholesterol and neutral sterol and acidic sterol in the feces of rats, to which the compounds of the present invention had been administered, were determined to monitor sterol balance and changes in the bile acid composition in feces. As a result, it was clarified that the administration of the compounds of the present invention resulted in an increase in sterols (in particular, bile acids) excreted into the feces. Further, the bile was sampled with the passage of time from rats having been subjected to cholangiostomy and bile acids thereof were determined. It was thus clarified that the administration of the compounds of the present invention significantly enhanced the excretion of bile acids into bile. Male Wistar rats weighting about 250 g were divided into groups each having 6 to 8 animals. Then these rats were fed with a standard feed for rat (CE-2; Nippon Crea Co., Ltd.) containing 2% of cholesterol for 10 days. During this period, 10 mg/kg of Compound-6 or Compound-5 suspended in an acacia solution was orally administered by force one a day. The feces were collected on the days 6 and 10. Then sterols were extracted therefrom in a conventional manner, acidic sterols and neutral sterols were determined. On the other hand, cholesterol in the feed was also determined so as to calculate the amount of feed-origin sterol.

TABLE 13

Effect of Compound-6 on sterol balance of rats

| Feed | Group | Serum total cholesterol (mg/dl) | Sterol (mg/200 g wt.) Intake | Sterol (mg/200 g wt.) Excretion | Biosynthesis in vivo (mg/200 g body wt.) | Sterol balance (mg) |
|---|---|---|---|---|---|---|
| Standard | Cont. | 77.7 ± 3.26 | 7.38 | 8.42 | 1.05 | 0 |
| | Cpd.-6 | 65.0 ± 2.98* | 7.48 | 10.81 | 1.05 | −2.26 |
| Containing cholesterol | Cont. | 91.2 ± 3.39 | 310.38 | 255.70 | 0 | +54.68 |
| | Cpd.-6 | 77.0 ± 2.19* | 301.45 | 275.52 | 0 | +25.93 |

*P < 0.05 in Student t-test (n = 6).

TABLE 14a

Standard feed

| Test group | Administration (days) | Cholesterol intake (mg/day) | Sterol in feces (mg/day) Copro-sterol | Sterol in feces (mg/day) Chole-sterol | Sterol in feces (mg/day) Acidic sterol | Sterol balance (mg/day) | excretion increase (mg/day) |
|---|---|---|---|---|---|---|---|
| Control | 5 | 7.93 | 3.40 | 2.85 | 2.59 | −0.91 | — |
| Cpd.-16 | | 8.28 | 3.98 | 3.51 | 5.19 | −4.40 | 3.49 |

TABLE 14a-continued

Standard feed

| Test group | Admini-stration (days) | Cholesterol intake (mg/day) | Sterol in feces (mg/day) | | | Sterol balance (mg/day) | excretion increase (mg/day) |
|---|---|---|---|---|---|---|---|
| | | | Copro-sterol | Chole-sterol | Acidic sterol | | |
| Control | 10 | 7.83 | 2.15 | 2.67 | 2.66 | +0.34 | — |
| Cpd.-16 | | 7.59 | 2.84 | 3.18 | 4.61 | −3.04 | 3.39 |

(n = 8)

TABLE 14b

High cholesterol feed

| Test group | Admini-stration (days) | Cholesterol intake (mg/day) | Sterol in feces (mg/day) | | | Sterol balance (mg/day) | excretion increase (mg/day) |
|---|---|---|---|---|---|---|---|
| | | | Copro-sterol | Chole-sterol | Acidic sterol | | |
| Control | 5 | 302.91 | 42.69 | 229.72 | 6.43 | +24.07 | — |
| Cpd.-16 | | 311.14 | 41.05 | 246.30 | 8.67 | +15.12 | 8.95 |
| Control | 10 | 350.28 | 59.06 | 222.47 | 6.17 | +62.59 | — |
| Cpd.-16 | | 329.80 | 58.27 | 233.08 | 9.93 | +28.52 | 34.07 |

(n = 8)

To examine the function mechanism of the compounds of the present invention for promoting bile acid excretion, an experiment was carried out to study the effect on a nuclear receptor LXR. It is assumed that LXR, which is a special nuclear receptor in the liver, might be a cholesterol sensor acting with 22-hydroxycholesterol as a ligand (Bethany A. Janowski at al., Nature 383:728–731, 1996). When cholesterol is accumulated in excess in a respective organ, LXR binds to the ligand, forms a heterodimer with RXR, and then binds to the hormone response element. This binding serves as a signal for promoting the oxidation of cholesterol into bile acid to be excreted from the body, thereby reducing deposited cholesterol. Accordingly, the liver is the organ which accumulates cholesterol in the largest amount and, at the same time, releases cholesterol as bile acid in the largest amount. It is estimated that the ability of the compounds of the present invention to promote the excretion of bile acid into feces would be established as follows. In the liver, RXR and LXR bind to the corresponding ligands, subsequently form a heterodimer with each other, and thus promote the expression of colesterol-7α-hydroxylase which is the rate-limiting enzyme in the biosynthesis pathway of bile acid. That is to say, it is estimated that the compounds of the present invention, ligands of RXR, would promote the transcription of the gene of colesterol-7α-hydroxylase (i.e., the enzyme of the rate state in the bile acid biosynthesis in the liver) and thus enhance the expression of colesterol-7α-hydroxylase. When the colesterol-7α-hydroxylase activity in the ground liver of rats to which Compound-6 according to the present invention had been orally administered was measured, it was confirmed that the enzymatic activity and yield of colesterol-7α-hydroxylase per unit protein weight were elevated dose-dependently. Accordingly, it can be concluded that the difference between the effects of clofibrate and the compounds of the present invention on cholesterol metabolism resides in that the former is a ligand of PPARα which is not capable of forming a heterodimer with LXR while the latter enhance the transcription of cholesterol oxidase gene RXR ligand-dependently and thus promote the excretion as bile acid from the body. These findings can be regarded as one major aspect of the present invention.

The experiment was carried out as follows. For each compound, 10 male Sprague Dawley rats weighing about 200 g were divided into 2 groups at random and fed for a week with a powdery rat feed (CE-2; Nippon Crea Co., Ltd.) containing 1% of cholesterol and drinking water ad libitum. The compounds of the present invention were suspended in a 2% acacia solution and orally administered by force once a day 7 times continuously in a dose of 5 mg/kg (Compound-1 and Compound-26) or 20 mg/kg (Compound-6 and Compound-14). In the early morning of the day 8, each animal was killed by blood loss. After refluxing with physiological saline, the liver was taken out immediately. Then 4 times as much 250 mM sucrose solution (containing 75 mM of nicotinamide, 1 mM of EDTA and 0.5 mM of $MgCl_2$) was added to the liver and the mixture was ground with the use of a Teflon homogenizer. Then the liquid ground matter was centrifuged at 9500G for 15 minutes at 4° C. and the mitochondria-free supernatant thus obtained was further centrifuged at 105000G for 60 minutes to thereby separate a microsome fraction. By using the microsome thus separated, the yield of 7α-cholesterol was measured in a conventional manner and the conversion rate was calculated.

TABLE 15

Effect of the compounds of the present invention on the formation of 7α-cholesterol in hepatic microsome

| Cpd. | Group | 7-α-Hydorxycholesterol (%) | 7-α-Hydorxycholesterol (nM/hr/mg protein) |
|---|---|---|---|
| Cpd.-1 | Control | 3.88 | 2.56 |
| | treated | 5.51 | 3.80 |

TABLE 15-continued

Effect of the compounds of the present invention
on the formation of 7α-cholesterol in hepatic microsome

| Cpd. | Group | 7-α-Hydorxycholesterol (%) | 7-α-Hydorxycholesterol (nM/hr/mg protein) |
|---|---|---|---|
| Cpd.-6 | Control | 4.24 | 2.69 |
|  | treated | 5.30 | 3.61 |
| Cpd.-14 | Control | 4.33 | 3.06 |
|  | treated | 7.06 | 4.47 |
| Cpd.-26 | Control | 2.89 | 2.05 |
|  | treated | 4.00 | 3.31 |

(n = 5), expressed in the average of 5 rats.

Example 13

Effect of Compound-14 on Potentiating Vitamin $D^3$ Activity

RXR also forms a heterodimer with a nuclear receptor, VDR, which acts with active vitamin $D_3$ (1a,25-dihydrocyvitamin $D_3$) as a ligand. However, no study has been made so far how the formation of this heterodimer means in vivo. Thus the effect of this heterodimer on gene transcription and, in its turn, its physiological meaning still remain unknown. Activated vitamin $D_3$ is essential for bone development and growth in children. Also, it is essential for preventing osteoporosis and bone fracture in aged and sick persons. In spite of such meaningful effects, studies have not been conducted to clarify the function of the heterodimer of VDR with RXR. The inventors studied calcium metabolism in db/db mice and the effect of Compound-14 on the calcium metabolism. This study was partly reported in 1992 (Tomoyoshi Hosokawa, Nogei Kagaku Kai-shi (J. Agr. Chem.), 66:1221–1226, 1992). Compared with normal litter of the same age, db/db mice show abnormally high levels of urinary calcium, blood calcium, blood calcitonin and parathyroid hormone. By administering an ascochlorin derivative, Compound-14, for 1 week, the urinary calcium, blood calcium and calcitonin levels were significantly lowered. By feeding db/db mice over a long time of period (4 weeks), it was found out that these animals suffered form a decrease in bone mineral density compared with normal litter of the same age. It is noteworthy that the decrease in the bone mineral density can be significantly prevented by administering the compound according to the present invention over a long time. In other words, the ascochlorin derivative which is a ligand of RXR potentiates the function of endogenous active vitamin $D_3$ dose-dependently to prevent calcium metabolic disorders such as osteoporosis. This effect of RXR ligands is a novel finding which has not been known until now.

Example 14

Phase I Clinical Test of Compound-6

A phase I clinical test of Compound-6, one of the compounds of the present invention, was carried out with 17 female and male patients aged 40 to 82 suffered from hypercholesterolemia. The experiment was continued for 12 weeks and Compound-6 was administered in the first 8 weeks. The dose was programmed as follows: 1 mg/kg till the 2nd week, 2 mg/kg till the 3rd week, 4 mg/kg till the 4th week, 8 mg/kg till the 6th week, and 16 mg/kg till the 8th week. From the 8th week to the 12th week (the placebo-administration period) a placebo was given without notifying the patients. The drug in a daily dose was divided into 3 portions and taken after meals. Each patient visited the hospital once a week and was subject to investigation and blood collection for analyzing serum.

In this test, no serious side effect, subjective or objective, was observed. Also no abnormality caused by the drug administration was observed in the data of the biochemical serum examination, blood percentage, urine examination, etc. Although vertigo arose in one patient, it was not so serious as to cease the drug administration. Since this patient also suffered from hypertension, it seemed that the normalization in blood pressure due to the administration of Compound-6 induced vertigo. No effect of the drug administration was observed in electrocardiography and ophthalmofundscopy too.

Figure 4:
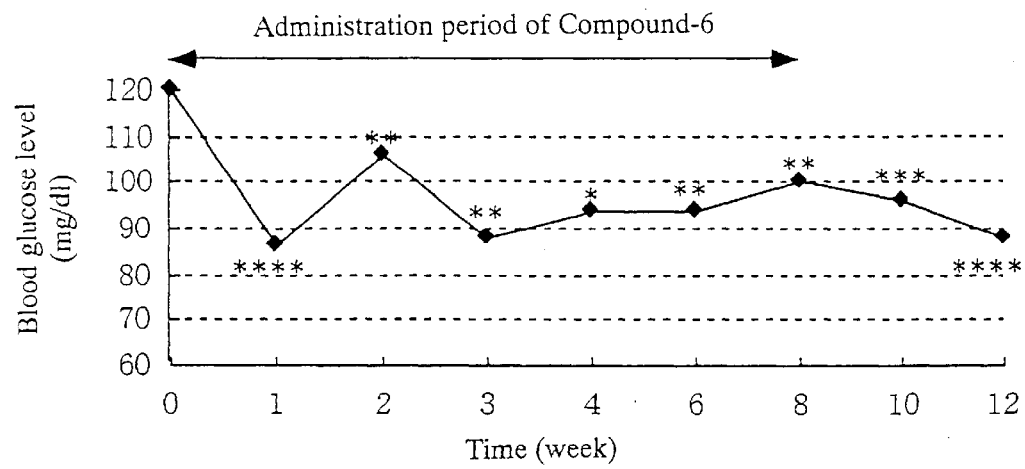
FIG. 4 shows changes in the fasting blood glucose level in a phase I clinical test of Compound-6.
Figure 5:
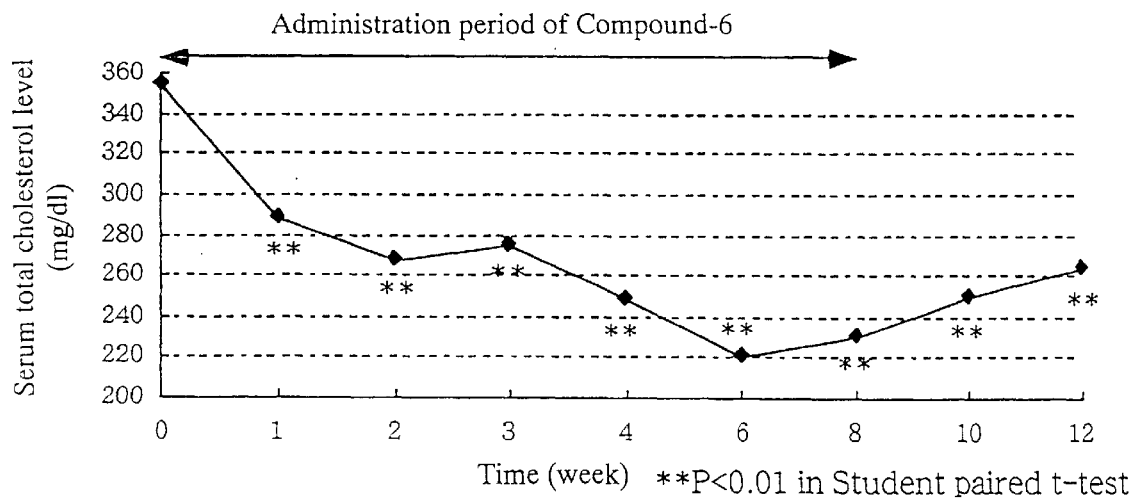
FIG. 5 shows decreases in the serum total cholesterol level in the phase I clinical test of Compound-6.

The largest change caused by the drug administration was a remarkable decrease in the serum total cholesterol level. This decrease initiated from 1 week after the administration and the decreasing rate was elevated with an increase in the administration dose, i.e., showing dose-dependency. It is further interesting that the serum total cholesterol level of the patients remained lower than the level before the administration even in 2 to 4 weeks after ceasing the drug administration. Namely, the drug clearly showed a carry-over effect. Although some of the patients suffered from hypertension or borderline hypertension in accordance with the standards specified by the WHO, both systolic blood pressure and diastolic blood pressure were lowered by administering Compound-6 in each group. The blood glucose levels of 5 diabetics included in the patients were each lowered to 100 mg/dl, i.e., the upper limit of the normal scope. On the other hand, the serum neutral fat level was not so remarkably lowered as the serum total cholesterol level. Although a significant decrease was observed exclusively in the group of patients with neutral fat/total cholesterol ratio of 1.5 or less, patients with the ratio of 1.5 or more showed no decrease in neutral fat (FIGS. 4 and 5).

These facts is accordant with the function mechanism where the compounds of the present invention form RXR: LXR heterodimers and thus activate the pathway of the excretion of cholesterol as bile acid from the body.

TABLE 16

Serum cholesterol-lowering effect of Compound-6 in humans (Mean ± SE)

| | Dose | Serum total cholesterol | | |
|---|---|---|---|---|
| | (mg.kg) | mg/dl | Decrease (%) | P |
| before treatment | — | 342 ± 61.0 | — | — |
| After 1 week | 0.5 | 273 ± 62.7 | −20 | P < 0.005 |
| After 2 weeks | 1 | 266 ± 66.7 | −22 | P < 0.002 |
| After 3 weeks | 2 | 269 ± 66.0 | −21 | P < 0.005 |
| After 4 weeks | 4 | 254 ± 65.7 | −28 | P < 0.0005 |
| After 6 weeks | 8 | 217 ± 58.8 | −36 | P < 0.0005 |
| After 8 weeks | 16 | 229 ± 61.5 | −33 | P < 0.0005 |
| After 10 weeks | 0 | 256 ± 57.6 | −25 | P < 0.0005 |
| After 12 weeks | 0 | 264 ± 57.7 | −22 | P < 0.002 |

Subjects: 11 males and 6 females aged from 48 to 70 (n = 17).
Placebo-administration period: 10th to 12th weeks.

Example 15

Phase II Clinical Test of Compound-6

A phase II clinical test of Compound-6 involving 30 patients suffered from noninsulin dependent diabetes (type II) was carried out. Compound-6 was administered in a daily dose of 6 mg/kg (i.e., administration of two tablets weighing 60 mg after each meal). The administration was continued for 12 weeks.

Figure 6:
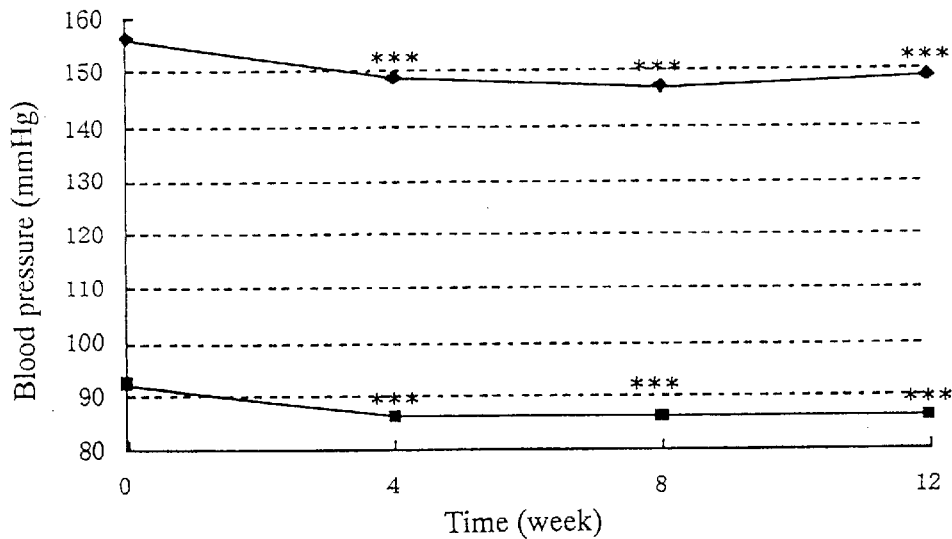
FIG. 6 shows the hypotensive effect on patients with borderline hypertension in the phase I clinical test of Compound-6.
Figure 7:
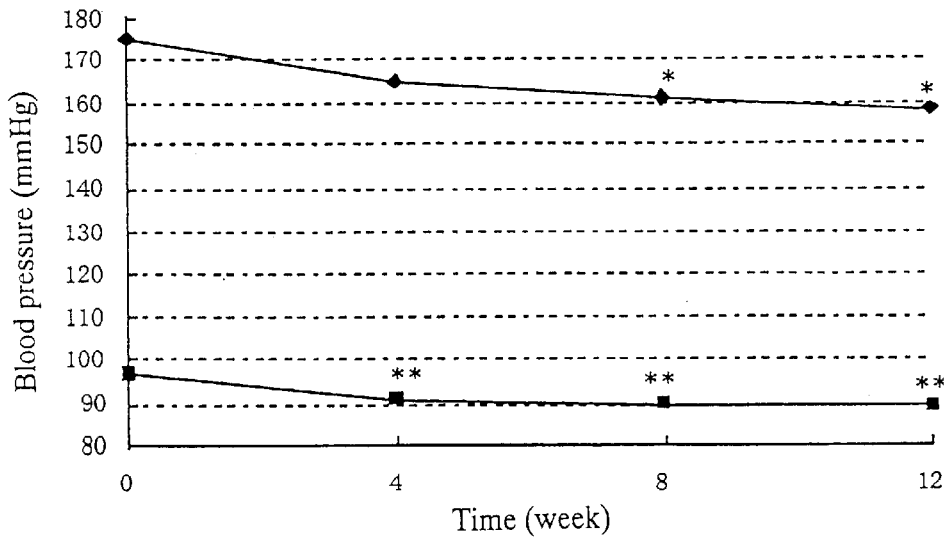
FIG. 7 shows the hypotensive effect on patients with hypertension in the phase I clinical test of Compound-6.

The facts clarified by this test are as follows. Compound-6 significantly lowered the blood glucose level and the serum total cholesterol level but showed little effect of lowering the serum neutral fat level. In a glucose tolerance test, wherein 50 g of glucose was orally loaded in a fasting state in early morning, Compound-6 significantly ameliorated the glucose tolerance and reduced the urinary glucose, compared with the data before the administration (FIGS. 6 and 7).

Figure 8:
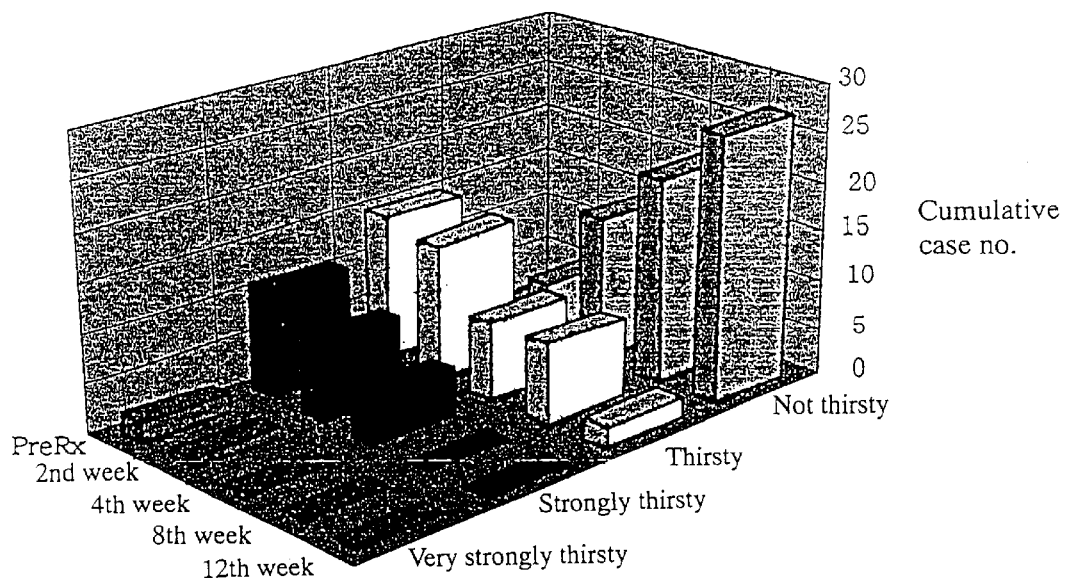
FIG. 8 shows amelioration of hydrodipsia with the passage of time in a phase II clinical test of Compound-6.

Accordingly, it has been proved that the compound of the present invention has an effect of ameliorating the metabolism and the insulin sensitivity in type II diabetes. Type II diabetes will be frequently associated with hypertension. In this test, 7 patients suffered form hypertension while 17 suffered from borderline hypertension in accordance with the WHO's standards. However, the blood pressure in these groups was significantly lowered by administering Compound-6. Troglitazone, which is a PPARγ ligand, ameliorates the insulin sensitivity, metabolic parameter and glucose tolerance in type II diabetes. However, it pools sodium in the body and thus exerts no hypotensive effect. Troglitazone clearly differs from the compounds of the present invention in this point (FIG. 8).

TABLE 17

Effects of Compound-6 of lowering fasting blood glucose level and serum total cholesterol level in phase II clinical test (dose of Compound-6: 360 mg/day)

a. Changes in blood glucose level (Mean ± SE)

| | n | Fasting blood glucose level (mg/dl) | Decrease (%) |
|---|---|---|---|
| Before treatment (Pre-Rx) | 30 | 188 ± 6.6 | — |
| 4th week | 30 | 165 ± 4.3** | 12.37 |
| 8th week | 30 | 159 ± 2.4** | 15.45 |
| 12th week | 30 | 154 ± 4.4** | 18.05 | b. Changes in serum total cholesterol level (Mean ± SE)

| | n | Serum total cholesterol level (mg/dl) | Decrease (%) |
|---|---|---|---|
| Before treatment (Pre-Rx) | 30 | 319 ± 10.2 | — |
| 4th week | 30 | 265 ± 4.4*** | 16.6 |
| 8th week | 30 | 240 ± 4.4*** | 24.3 |
| 12th week | 30 | 231 ± 4.4*** | 27.2 |

(n = 30), P < 0.01 and *P < 0.001 in Student's paired t-test.

In the clinical test of Compound-6 as described above, it is most outstanding that clinical symptoms of complication of diabetes caused by diabetic nephropathy and diabetic neuropathy were significantly ameliorated. Most diabetics, for example, experience thirst, which is caused by diabetic nephropathy, and also the symptom of polyuria, which is caused by excessive intake of water. Compound-6 ameliorated these symptoms in the group of patients.

The 30 patients with type II diabetes were inquired about thirsty and evaluated in 4 grades, namely, (+++) very strongly thirsty; (++) strongly thirsty; (+) thirsty; and (−) not thirsty. As FIG. 8 clearly shows, the conditions were ameliorated as the treatment with Compound-6 proceeded (2nd week: P,0.005, 4th week: P<0.005, 8th week: P<0.001, 12th week: P<0.001, compared with the data before the initiation of the treatment). The treatment ratio amounted to 100%.

Since type II diabetes is a typical chronic disease, it is not uncommon for patients to have suffered from this disease for 15 to 20 years. Such patients with a prolonged case history would not respond to most drugs. Among the patients involved in this experiment, 8 persons had suffered from the disease for over 15 to 20 years. It is noteworthy that the symptoms of thirst and polyuria were ameliorated in all cases in spite of this fact. The level of urinary glucose, which was measured by collecting urine for 24 hours, was also significantly reduced by administering Compound-6. Moreover, symptoms caused by diabetic neuropathy (for example, "sluggishness", "feebleness", "boredom", "leg muscular pain") were significantly ameliorated. Complications of diabetes may be considered as falling within the category of chronic inflammation. It is considered that the effects of the compounds of the present invention of ameliorating complication of diabetes depend on not the action of ameliorating metabolism but the function mechanism of the anti-inflammatory drug effect on chronic inflammation.

TABLE 18a

Amelioration of boredom of type II diabetics by the administration of Compound-6

| Boredom | Immediately before administration | 4th week | 8th week | 12th week | Total |
|---|---|---|---|---|---|
| Yes | 14 | 10 | 2 | 0 | 26 |
| No | 1 | 5 | 13 | 15 | 34 |
| Total | 15 | 15 | 15 | 15 | 60 |

TABLE 18b

Amelioration of feebleness of type II diabetics by the administration of Compound-6

| Feebleness | Immediately before administration | 4th week | 8th week | 12th week | Total |
|---|---|---|---|---|---|
| Yes | 25 | 15 | 6 | 1 | 47 |
| No | 0 | 10 | 19 | 24 | 53 |
| Total | 25 | 25 | 25 | 25 | 100 |

TABLE 18c

Amelioration of neuralgia of type II diabetics by the administration of Compound-6

| Neuralgia | Immediately before administration | 4th week | 8th week | 12th week | Total |
|---|---|---|---|---|---|
| Yes | 12 | 7 | 6 | 2 | 27 |
| No | 4 | 9 | 10 | 14 | 37 |
| Total | 16 | 16 | 16 | 16 | 64 |

Example 16

Formation of Schiff Bases of Compounds of the Present Invention with Serum Proteins The compounds of the present invention quickly react with free amino groups of serum proteins to form reversible Schiff bases both in vivo and in vitro. Although the compounds of the present invention show retinoid-like effects, they would not exhibit such strong toxicity as retinoids. This is because the compounds of the present invention react with serum proteins and are converted into Schiff bases in the course of the absorption via the intestinal tract so that the biological activities are masked. On the other hand, the reaction of forming Schiff basses between the compounds of the present invention and amino groups of proteins also quickly proceeds in vitro in a neutral or weak alkaline aqueous solution. It is known that Compound-1 and Compound-26, among the compounds of the present invention, show a strong toxicity when present in a free state in the blood. For example, an acetylated derivative of Compound-1 (4-O-acetylascochlorin: Compound-5) is insoluble in water but can be solubilized in water to give a transparent liquid by using a surfactant HCO-60. In this state, Compound-5 molecules are not dissolved in water but dispersed as fine micelles smaller than the visible ray wavelength. Thus, the liquid becomes transparent. When orally administered to an animal in this state, Compound-5 is quickly absorbed via the digestive tract. When Compound-2 was administered to a rat only in a small dose (2 mg/kg), the blood pressure was lowered and the heart stopped within 1 to 2 hours. When the absorption kinetics were monitored by collecting the blood with the passage of time, not Compound-5 but Compound-1 was present in the serum. This is because Compound-5 absorbed via the digestive tract is immediately decomposed by acylase in the blood. Namely, it is understood that free ascochlorin present in vivo is strongly toxicity to the circulatory system. However, a rat was not killed by administering Compound-5 suspended in a 2% acacia solution even at a dose larger by 100 times (i.e., 200 mg/kg). When the rat blood was collected with the passage of time, no free Compound-1 was detected in the blood. However, the fact that no free Compound-1 was detected in the blood does not indicate that Compound-1 was not present in the blood. On the contrary, it can be proved that Compound-1 was present in the blood of the rat, to which Compound-5 had been administered, at such a high level as to exceed a lethal dose in the case of the free compound.

To the serum of the rat to which Compound-5 had been administered as a suspension, 10 times as much acetonitrile containing 1% of acetic acid was added and the mixture was allowed to stand at room temperature for 1 week. In case of a drug molecule binds to protein, the drug molecule usually binds only weakly to the protein via a non-covalent bond (for example, hydrophobic bond, hydrogen bond, van der Waals bond, ion-dipole moment bond, etc.). Accordingly, the drug can be dissociated from the protein by adding an organic solvent and allowing it to stand for about 1 hour. However, ascochlorin present in the serum of the rat, to which Compound-5 had been administered, would be never released from the protein after 1 hour. To almost completely recover ascochlorin binding to the protein, it was required to allow the mixture to stand at room temperature for 1 week. Moreover, ascochlorin was not dissociated merely by adding an organic solvent (acetonitrile, ethanol, acetone, etc.) to the serum of the rat to which Compound-5 had been administered. Namely, it was not released until the mixture was acidified by adding acetic acid. Based on these facts, it was estimated that ascochlorin present in the blood might form a Schiff base via covalent bond to the amino group of serum protein. In the formation of a Schiff base by the reaction between aldehyde group and amino group, the equilibrium shifts toward the base formation under alkaline conditions and toward the dissociation under acidic conditions. To release ascochlorin binding to the serum protein via covalent bond, it is therefore necessary to shift the equilibrium toward the left side by acidification.

Subsequently, Compound-6 was added to the serum to examine the formation of a Schiff base in vitro. Compound-6 is hardly soluble in water and shows a solubility of $0.8\ \mu g/ml$ in phosphate buffer saline (PBS). When Compound-6 dissolved in dimethyl sulfoxide at a high concentration was added in portions to bovine serum, Compound-6 was dissolved in the serum at a ratio of 800 mg/ml (i.e., 1000-fold) and the serum turned yellow depending on the concentration of Compound-6. When an organic solvent (ethanol, acetonitrile, etc.) was added to this yellow serum, the coloring matter was not dissolved in the organic solvent but precipitated as yellow serum protein. The organic solvent layer contained no Compound-6. However, Compound-6 was quantitatively recovered as an acetonitrile solution by adding acetonitrile containing 1% of acetic acid to this yellow precipitate and allowing the mixture to stand for 1 week. In a reaction between a protein and a drug molecule, there has been taken no consideration into the conversion into a novel compound via the formation of a covalent bond between the drug and serum protein in vivo. However, it is obvious that aldehyde group in the benzene ring of the compounds of the present invention and amino group of serum protein form a Schiff base on the basis of the following facts. (1) The compounds of the present invention cannot be detected by any usual methods from the serum of animals to which the compounds have been administered. (2) The compounds of the present invention are released by adding an acidified organic solvent in a large amount to the serum and allowing to stand at room temperature for about 1 week. (3) When added to serum in vitro, the compounds of the present invention are dissolved at a ratio as high as 1000-fold and can be recovered by the same method as used in recovering the compounds of the present invention from the serum of animals to which the compounds have been administered. (4) The serum of animals, to which the compounds have been administered, or serum containing the compounds of the present invention turns into yellow. (Namely, the absorption assignable to aldehyde group disappears but another absorption assignable to Schiff base appears.) That is to say, the compounds of the present invention are characterized by forming Schiff bases with the amino group of serum protein as the essential requirement of the invention.

The Schiff bases formed in vivo by the compounds of the present invention with serum protein are mask compounds which are not directly incorporated into cells and thus exhibit no biological activity (drug effect or toxicity) quickly. To establish the biological activity, such a Schiff base should be incorporated into vesicles in cells via endocytosis and hydrolyzed in the protein moiety to thereby regenerate the compounds of the present invention in a free state. Accordingly, the administration of the compounds of the present invention is equivalent to the administration of compounds the biological activity of which has been masked and which shows a slow action and no side effects.

Test with the Use of Rats

Figure 9:
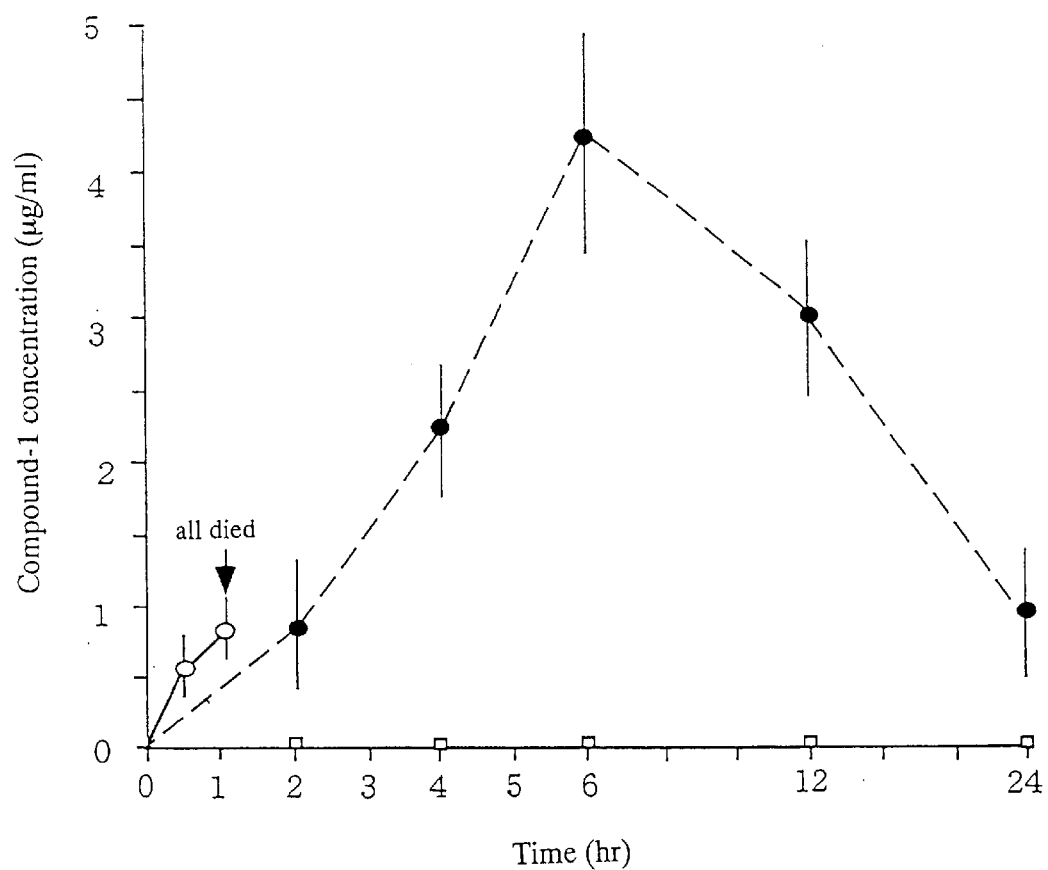
FIG. 9 shows the concentration in the blood of Compound-1 orally administered to rats.

Male Wistar rats (n=4) weighing about 200 g were employed and the concentration of Compound-1 contained in the serum was expressed in mean±SE (FIG. 9).

In FIG. 9, open circles show a case wherein Compound-5 was solubilized with HCO-60 and orally administered in a dose of 2 mg/kg. As FIG. 9 shows, Compound-5 was quickly absorbed via the digestive tract and hydrolyzed by acylase in the blood to give Compound-1. When free Compound-1 appeared at the concentration as shown in FIG. 9, however, all of the rats died within 1 hour following administration.

Solid circles show a case wherein Compound-5 was suspended in an acacia solution and orally administered in a dose of 20 mg/kg. Per part of the serum collected with the passage of time, ethanol containing 1% of acetic acid was added and the mixture was allowed to stand in the dark at room temperature for 7 days. Then Compound-1 was determined by high performance liquid chromatography.

Open squares show a case wherein Compound-5 was suspended in an acacia solution and orally administered. Then the blood was collected at definite points and Compound-1 was determined by high performance liquid chromatography immediately thereafter. No Compound-1 was detected in this case. Separately, Compound-5 suspended in an acacia solution was orally administered to rats having been cannulated into the portal vein. Then the portal blood was collected with the passage of time and Compound-1 was determined. Similar to the case as FIG. 8 shows, no free Compound-1 was present in the serum. Namely, Compound-1 was all in the form of Schiff base type compound released after allowing to stand in ethanol containing acetic acid for 1 week.

Reaction of Compounds of the Present Invention with Serum

Compound-14, Compound-5 and Compound-6 were each dissolved in polyethylene glycol-400, then added to bovine serum to give a concentration of 500 μg/ml and allowed to stand at room temperature. At definite points, the serum was sampled and divided into 2 portions. Ten times as much acetonitrile was added to one of these portions and the mixture was centrifuged. Then the free compound in the serum was determined. To the other portion, 10 times as much acetonitrile containing 1% of acetic acid was added. After allowing to stand at room temperature for 1 week, the mixture was centrifuged and the free compound was determined (FIG. 10).

Figure 10:
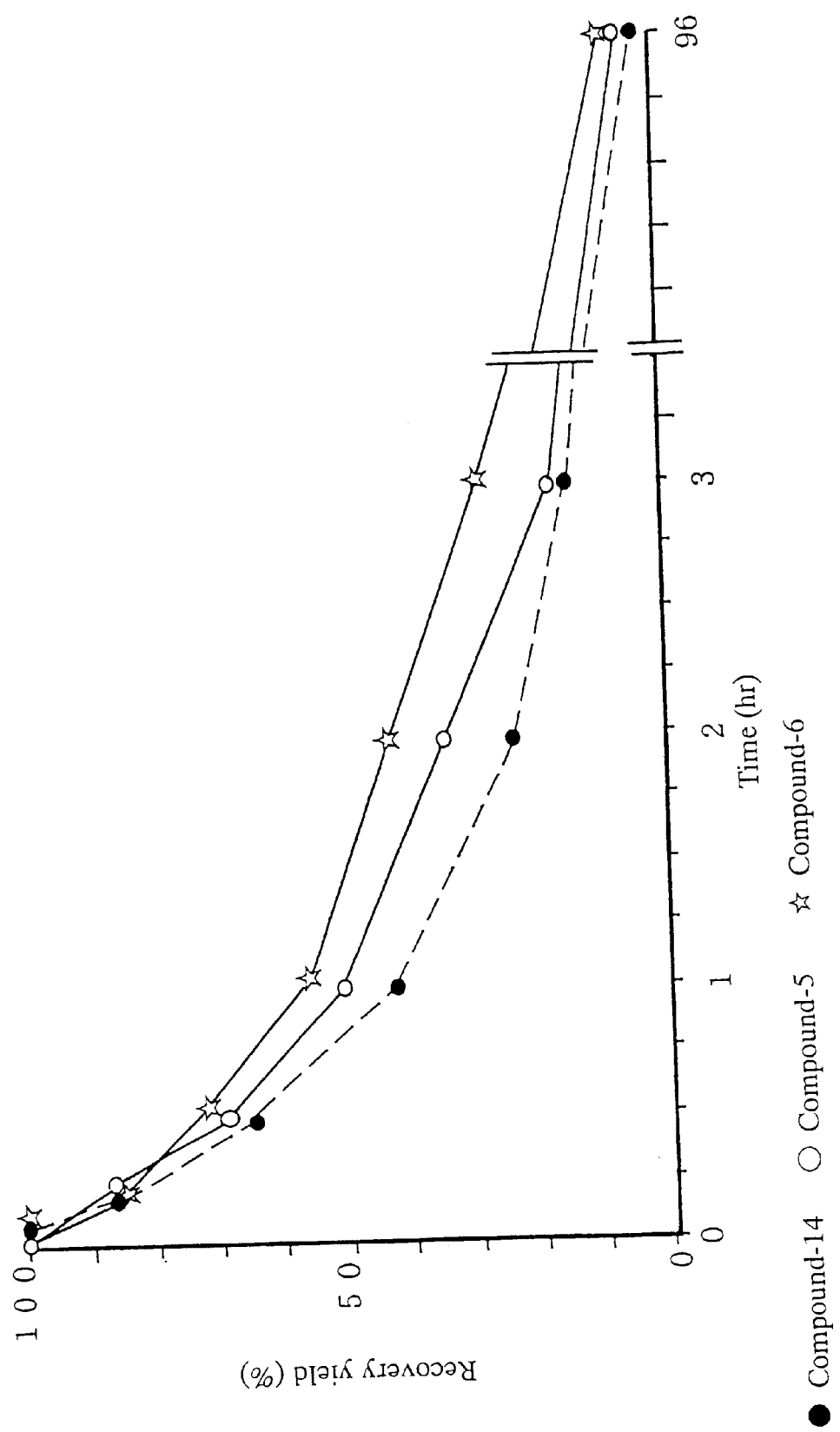
FIG. 10 shows the decrease in free form of the compounds according to the present invention added to bovine serum wherein solid circles, open circles and squares stand respectively for Compound 14, 5 and 6.

As FIG. 10 clearly shows, each compound remaining in the serum deproteinized by adding acetonitrile was decreased with the passage of time. However, this decrease was merely an apparent one. In the case where acetonitrile containing 1% of acetic acid was added to the serum and the mixture was allowed to stand at room temperature for 1 week followed by determination, each compound was recovered at a yield of 98 to 102%. In the case of Compound-5, which is an acylated derivative being hydrolyzed in the period of allowing to stand at room temperature to give Compound-1, the level was determined by calculating the conversion level of Compound-5 based on the obtained level each of both compounds. On the other hand, Compound-6 and Compound-14 could be almost quantitatively recovered in the centrifuged supernatant after adding acetonitrile containing 1% of acetic acid and allowed to stand at room temperature for 1 week.

What is claimed is:

1. A method for treating a disease or condition in a mammal which can be alleviated by the retinoid X receptor ligand (RXRL)-dependent regulation of gene transcription or inhibiting the infiltration of leukocytes into damaged arteries, wherein said disease or condition in a mammal which can be alleviated by the RXRL-dependent regulation of gene transcription, is arteriosclerosis in a human induced by serum cholesterol; wherein said method comprises:

administering to said mammal a compound capable of acting as a retinoid X receptor ligand or a pharmaceutically acceptable salt thereof in an amount effective for treating said disease or condition or inhibiting the infiltration of leukocytes into damaged arteries, together with a pharmaceutically acceptable additive, wherein said compound is selected from the group consisting of:

compounds of formula (1)

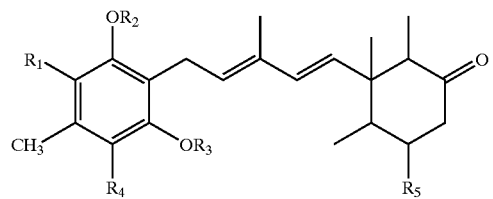

wherein

| # | $R_1$ | $R_2$ | $R_3$ | $R_4$ | $R_5$ |
|---|---|---|---|---|---|
| 1 | —CHO | H | H | Cl | H |
| 2 | —CHO | H | H | Cl | —OAc |
| 3 | —CHO | H | H | Br | H |
| 4 | —CHO | H | H | H | H |
| 5 | —CHO | H | $CH_3CO$— | Cl | H |
| 6 | —CHO | H | —$CH_3$ | Cl | H |
| 7 | —CHO | —$CH_3$ | —$CH_3$ | Cl | H |
| 8 | —CHO | $CH_3CO$— | —$CH_3$ | Cl | H |
| 9 | —CHO | —$CH_3$ | $CH_3CO$— | Cl | H |
| 10 | —CHO | —$CH_3$ | H | Cl | H |
| 11 | —CHO | H | $CH_3CH_2$— | Cl | H |
| 12 | —CHO | H | allyl | Cl | H |
| 13 | —CHO | H | butyl | Cl | H |
| 14 | —CHO | H | —$CH_2COOH$ | Cl | H |
| 15 | —CHO | H | —$(CH_2)_2COOH$ | Cl | H |
| 16 | —CHO | H | —$(CH_2)_3COOH$ | Cl | H |
| 17 | —CHO | H | —$(CH_2)_4COOH$ | Cl | H |
| 18 | —CHO | H | —$CH_2COOCH_3$ | Cl | H |
| 19 | —CHO | H | nicotinoyl | Cl | H |
| 20 | —CHO | H | benzoyl | Cl | H |
| 21 | —CHO | H | isonicotinoyl | Cl | H | compounds of formula (2)

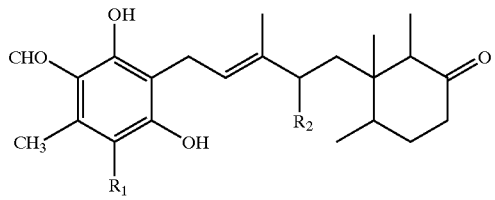

wherein

| # | $R_1$ | $R_2$ |
|---|---|---|
| 22 | Cl | H |
| 23 | H | H |
| 24 | Cl | —OH |
| 25 | Cl | —OAc | a compound of formula (3)

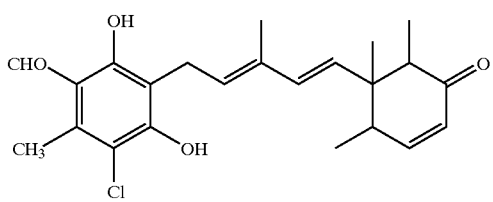

a compound of formula (4)

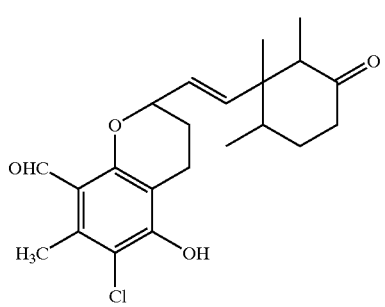

a compound of formula (5)

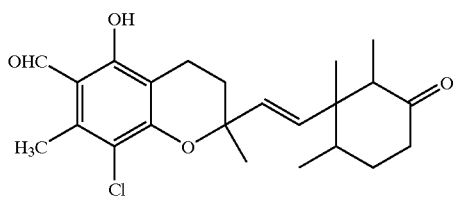

compounds of formula (6)

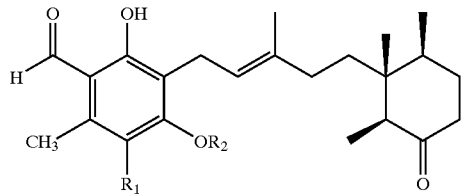

wherein

| # | R₁ | R₂ |
|---|----|----|
| 29 | Cl | H |
| 30 | Cl | —CH₃ |
| 31 | Cl | CH₃CO— |
| 32 | H | H |
| 33 | H | —CH₃ |
| 34 | H | CH₃CO— | and compounds of formula (7)

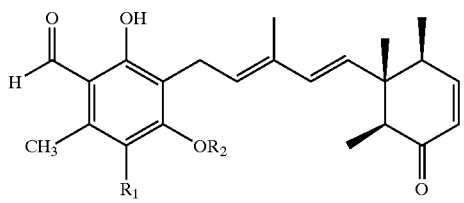

wherein

| # | R₁ | R₂ |
|---|----|----|
| 35 | Cl | H |
| 36 | Cl | —CH₃ |
| 37 | Cl | CH₃CO— |
| 38 | H | H |
| 39 | H | —CH₃ |
| 40 | H | CH₃CO—. |

2. A method for treating a disease or condition in a mammal which can be alleviated by the retinoid X receptor ligand (RXRL)-dependent regulation of gene transcription or inhibiting the infiltration of leukocytes into damaged arteries, wherein said disease or condition in a mammal which can be alleviated by the RXRL-dependent regulation of gene transcription, is arteriosclerosis by hypertension, cerebral angiopathy, arterial restenosis following percutaneous transluminal coronary angioplasty, or arteriocapillary sclerosis, or arteriosclerosis in transplanted organs; wherein said method comprises:
administering to said mammal a compound capable of acting as a retinoid X receptor ligand or a pharmaceutically acceptable salt thereof in an amount effective for treating said disease or condition or inhibiting the infiltration of leukocytes into damaged arteries, together with a pharmaceutically acceptable additive, wherein said compound is selected from the group consisting of:
compounds of formula (1)

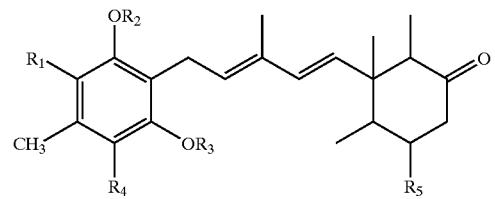

wherein

| # | R₁ | R₂ | R₃ | R₄ | R₅ |
|---|----|----|----|----|----|
| 1 | —CHO | H | H | Cl | H |
| 2 | —CHO | H | H | Cl | —OAc |
| 3 | —CHO | H | H | Br | H |
| 4 | —CHO | H | H | H | H |
| 5 | —CHO | H | CH₃CO— | Cl | H |
| 6 | —CHO | H | —CH₃ | Cl | H |
| 7 | —CHO | —CH₃ | —CH₃ | Cl | H |
| 8 | —CHO | CH₃CO— | —CH₃ | Cl | H |

| # | R$_1$ | R$_2$ | R$_3$ | R$_4$ | R$_5$ |
|---|---|---|---|---|---|
| 9 | —CHO | —CH$_3$ | CH$_3$CO— | Cl | H |
| 10 | —CHO | —CH$_3$ | H | Cl | H |
| 11 | —CHO | H | CH$_3$CH$_2$— | Cl | H |
| 12 | —CHO | H | allyl | Cl | H |
| 13 | —CHO | H | butyl | Cl | H |
| 14 | —CHO | H | —CH$_2$COOH | Cl | H |
| 15 | —CHO | H | —(CH$_2$)$_2$COOH | Cl | H |
| 16 | —CHO | H | —(CH$_2$)$_3$COOH | Cl | H |
| 17 | —CHO | H | —(CH$_2$)$_4$COOH | Cl | H |
| 18 | —CHO | H | —CH$_2$COOCH$_3$ | Cl | H |
| 19 | —CHO | H | nicotinoyl | Cl | H |
| 20 | —CHO | H | benzoyl | Cl | H |
| 21 | —CHO | H | isonicotinoyl | Cl | H | compounds of formula (2)

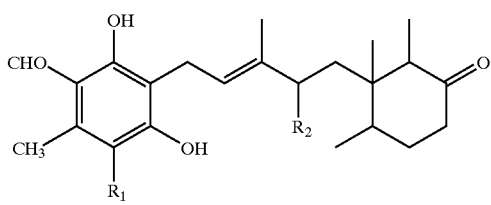

wherein

| # | R$_1$ | R$_2$ |
|---|---|---|
| 22 | Cl | H |
| 23 | H | H |
| 24 | Cl | —OH |
| 25 | Cl | —OAc | a compound of formula (3)

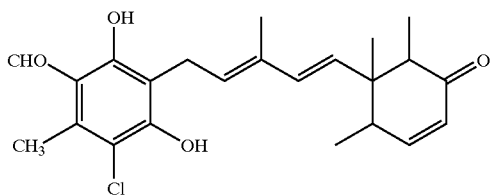

a compound of formula (4)

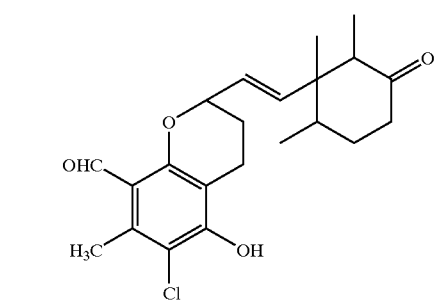

a compound of formula (5)

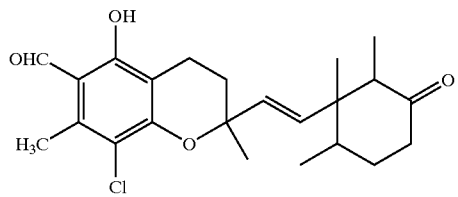

compounds of formula (6)

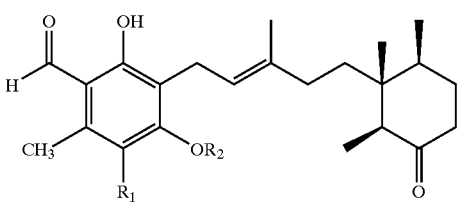

wherein

| # | R$_1$ | R$_2$ |
|---|---|---|
| 29 | Cl | H |
| 30 | Cl | —CH$_3$ |
| 31 | Cl | CH$_3$CO— |
| 32 | H | H |
| 33 | H | —CH$_3$ |
| 34 | H | CH$_3$CO— | and compounds of formula (7)

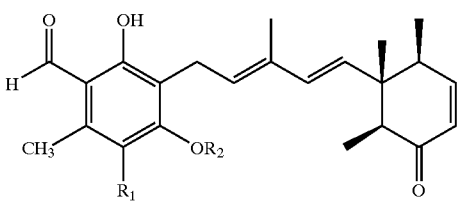

wherein

| # | R$_1$ | R$_2$ |
|---|---|---|
| 35 | Cl | H |
| 36 | Cl | —CH$_3$ |
| 37 | Cl | CH$_3$CO— |
| 38 | H | H |
| 39 | H | —CH$_3$ |
| 40 | H | CH$_3$CO—. |

3. A method for treating a disease or condition in a mammal which can be alleviated by the RXRL-dependent regulation of gene transcription,
wherein said disease or condition which can be alleviated by the RXRL-dependent regulation of gene transcription is type II diabetes in a human; wherein said method comprises:
administering to said human a compound capable of acting as a retinoid X receptor ligand or a pharmaceutically acceptable salt thereof in an amount effective for treating said disease or condition, together with a pharmaceutically acceptable additive, wherein said compound is selected from the group consisting of:

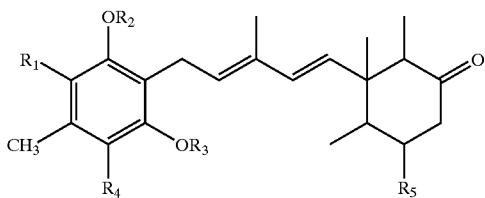

wherein

| # | $R_1$ | $R_2$ | $R_3$ | $R_4$ | $R_5$ |
|---|---|---|---|---|---|
| 1 | —CHO | H | H | Cl | H |
| 2 | —CHO | H | H | Cl | —OAc |
| 3 | —CHO | H | H | Br | H |
| 4 | —CHO | H | H | H | H |
| 5 | —CHO | H | $CH_3CO$— | Cl | H |
| 6 | —CHO | H | —$CH_3$ | Cl | H |
| 7 | —CHO | —$CH_3$ | —$CH_3$ | Cl | H |
| 8 | —CHO | $CH_3CO$— | —$CH_3$ | Cl | H |
| 9 | —CHO | —$CH_3$ | $CH_3CO$— | Cl | H |
| 10 | —CHO | —$CH_3$ | H | Cl | H |
| 11 | —CHO | H | $CH_3CH_2$— | Cl | H |
| 12 | —CHO | H | allyl | Cl | H |
| 13 | —CHO | H | butyl | Cl | H |
| 20 | —CHO | H | benzoyl | Cl | H | compounds of formula (2)

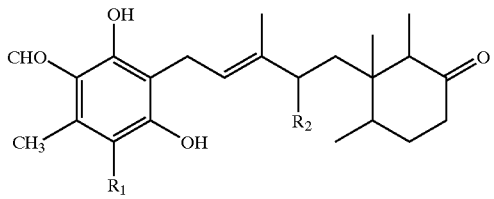

wherein

| # | $R_1$ | $R_2$ |
|---|---|---|
| 22 | Cl | H |
| 23 | H | H |
| 24 | Cl | —OH |
| 25 | Cl | —OAc | a compound of formula (3)

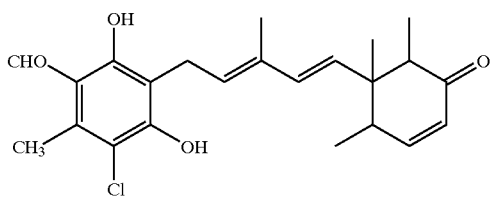

a compound of formula (4)

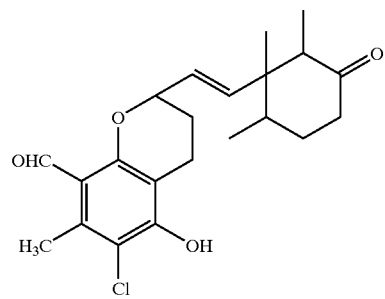

a compound of formula (5)

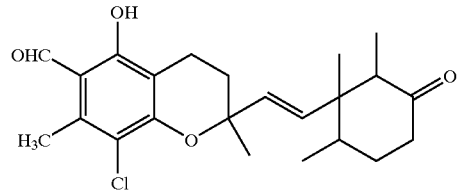

compounds of formula (6)

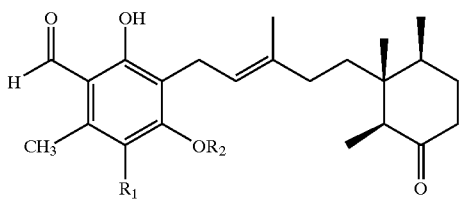

wherein

| # | $R_1$ | $R_2$ |
|---|---|---|
| 29 | Cl | H |
| 30 | Cl | —$CH_3$ |
| 31 | Cl | $CH_3CO$— |
| 32 | H | H |
| 33 | H | —$CH_3$ |
| 34 | H | $CH_3CO$— | and compounds of formula (7)

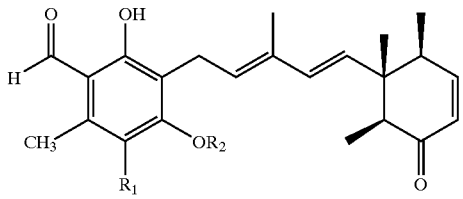

wherein

| # | $R_1$ | $R_2$ |
|---|---|---|
| 35 | Cl | H |
| 36 | Cl | —$CH_3$ |

-continued

| # | R₁ | R₂ |
|---|---|---|
| 37 | Cl | CH₃CO— |
| 38 | H | H |
| 39 | H | —CH₃ |
| 40 | H | CH₃CO— |

4. A method for treating a disease or condition in a mammal which can be alleviated by the RXRL-dependent regulation of gene transcription, wherein said disease or condition which can be alleviated by the RXRL-dependent regulation of gene transcription is degeneration and/or necrosis of pancreatic Langerhans' islet β-cells; wherein said method comprises:
administering to said human a compound capable of acting as a retinoid X receptor ligand or a pharmaceutically acceptable salt thereof in an amount effective for treating said disease or condition, together with a pharmaceutically acceptable additive, wherein said compound selected from the group consisting of:

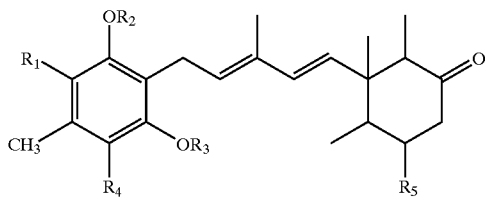

wherein

| # | R₁ | R₂ | R₃ | R₄ | R₅ |
|---|---|---|---|---|---|
| 1 | —CHO | H | H | Cl | H |
| 2 | —CHO | H | H | Cl | —OAc |
| 3 | —CHO | H | H | Br | H |
| 4 | —CHO | H | H | H | H |
| 5 | —CHO | H | CH₃CO— | Cl | H |
| 6 | —CHO | H | —CH₃ | Cl | H |
| 7 | —CHO | —CH₃ | —CH₃ | Cl | H |
| 8 | —CHO | CH₃CO— | —CH₃ | Cl | H |
| 9 | —CHO | —CH₃ | CH₃CO— | Cl | H |
| 10 | —CHO | —CH₃ | H | Cl | H |
| 11 | —CHO | H | CH₃CH₂— | Cl | H |
| 12 | —CHO | H | allyl | Cl | H |
| 13 | —CHO | H | butyl | Cl | H |
| 14 | —CHO | H | —CH₂COOH | Cl | H |
| 15 | —CHO | H | —(CH₂)₂COOH | Cl | H |
| 16 | —CHO | H | —(CH₂)₃COOH | Cl | H |
| 17 | —CHO | H | —(CH₂)₄COOH | Cl | H |
| 18 | —CHO | H | —CH₂COOCH₃ | Cl | H |
| 19 | —CHO | H | nicotinoyl | Cl | H |
| 20 | —CHO | H | benzoyl | Cl | H |
| 21 | —CHO | H | isonicotinoyl | Cl | H | compounds of formula (2)

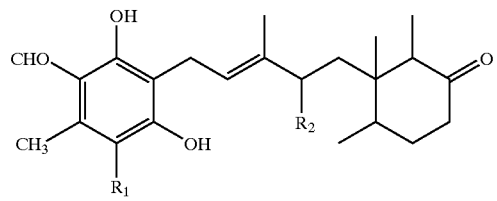

wherein

| # | R₁ | R₂ |
|---|---|---|
| 22 | Cl | H |
| 23 | H | H |
| 24 | Cl | —OH |
| 25 | Cl | —OAc | a compound of formula (3)

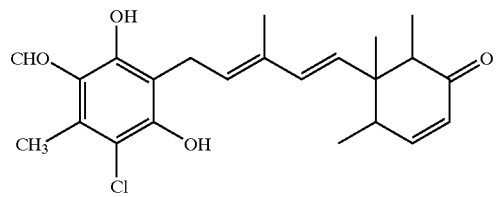

a compound of formula (4)

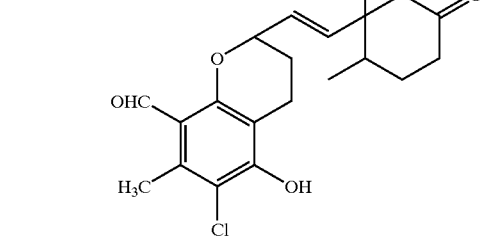

a compound of formula (5)

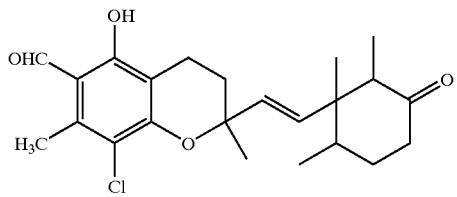

compounds of formula (6)

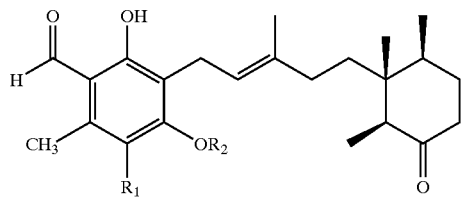

wherein

| # | R₁ | R₂ |
|---|----|----|
| 29 | Cl | H |
| 30 | Cl | —CH₃ |
| 31 | Cl | CH₃CO— |
| 32 | H | H |
| 33 | H | —CH₃ |
| 34 | H | CH₃CO— | and compounds of formula (7)

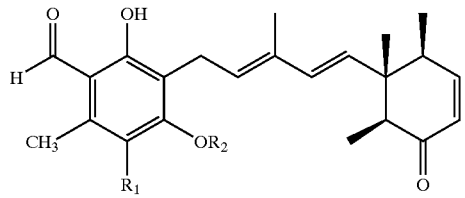

wherein

| # | R₁ | R₂ |
|---|----|----|
| 35 | Cl | H |
| 36 | Cl | —CH₃ |
| 37 | Cl | CH₃CO— |
| 38 | H | H |
| 39 | H | —CH₃ |
| 40 | H | CH₃CO—. |

5. A pharmaceutical composition for treating a disease or condition in a mammal which can be alleviated by the retinoid X receptor ligand (RXRL)-dependent regulation of gene transcription, wherein said pharmaceutical composition comprises:

a compound capable of acting as a retinoid X receptor ligand or a pharmaceutically acceptable salt thereof in an amount effective for treating said disease or condition, wherein said compound is selected from the group consisting of: compounds of formula (1)

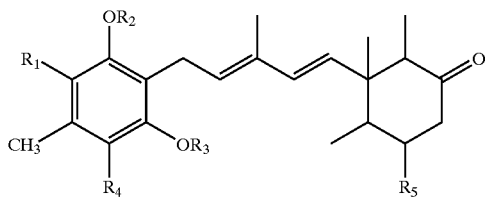

wherein

| # | R₁ | R₂ | R₃ | R₄ | R₅ |
|---|----|----|----|----|----|
| 2 | —CHO | H | H | Cl | —OAc |
| 3 | —CHO | H | H | Br | H |
| 4 | —CHO | H | H | H | H |
| 5 | —CHO | H | CH₃CO— | Cl | H |
| 7 | —CHO | —CH₃ | —CH₃ | Cl | H |
| 8 | —CHO | CH₃CO— | —CH₃ | Cl | H |
| 9 | —CHO | —CH₃ | CH₃CO— | Cl | H |
| 10 | —CHO | —CH₃ | H | Cl | H |
| 12 | —CHO | H | allyl | Cl | H |
| 20 | —CHO | H | benzoyl | Cl | H | compounds of formula (2)

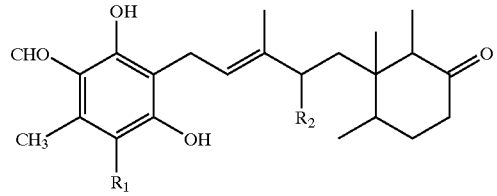

wherein

| # | R₁ | R₂ |
|---|----|----|
| 22 | Cl | H |
| 23 | H | H |
| 24 | Cl | —OH |
| 25 | Cl | —OAc | a compound of formula (3)

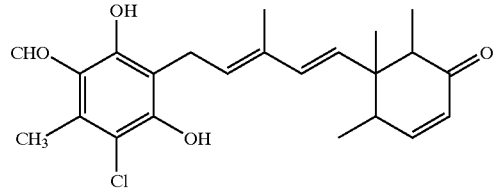

a compound of formula (4)

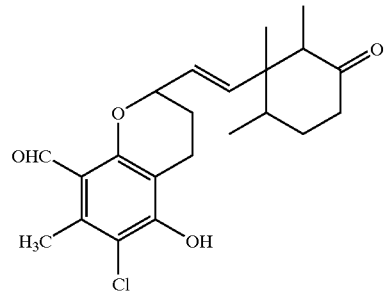

a compound of formula (5)

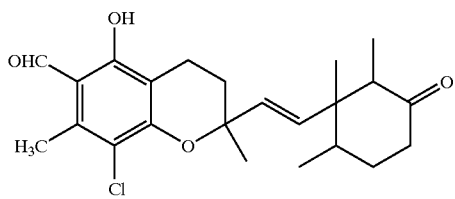

compounds of formula (6)

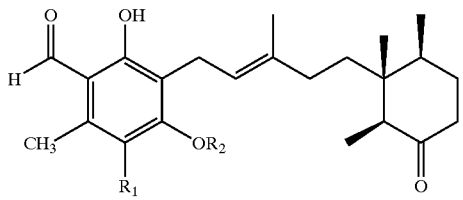

wherein

| # | R$_1$ | R$_2$ |
|---|---|---|
| 29 | Cl | H |
| 30 | Cl | —CH$_3$ |
| 31 | Cl | CH$_3$CO— |
| 32 | H | H |
| 33 | H | —CH$_3$ |
| 34 | H | CH$_3$CO— | and compounds of formula (7)

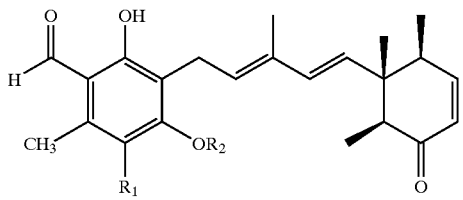

wherein

| # | R$_1$ | R$_2$ |
|---|---|---|
| 35 | Cl | H |
| 36 | Cl | —CH$_3$ |
| 37 | Cl | CH$_3$CO— |
| 38 | H | H |
| 39 | H | —CH$_3$ |
| 40 | H | CH$_3$CO— |

; and
  a pharmaceutically acceptable additive, wherein said additive is a synthetic aliphatic surfactant or a polymer substance soluble in organic solvents.

6. A pharmaceutical composition for treating a disease or condition in a mammal which can be alleviated by the retinoid X receptor ligand (RXRL)-dependent regulation of gene transcription, wherein said pharmaceutical composition comprises:
  a compound capable of acting as a retinoid X receptor ligand or pharmaceutically acceptable salt thereof in an amount effective for treating said disease or condition,
  wherein said compound is selected from the group consisting of:

compounds of formula (1)

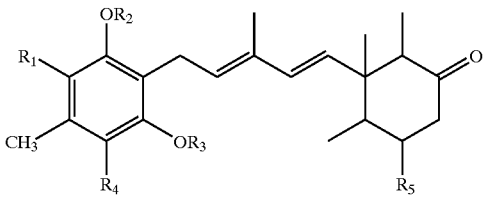

wherein

| # | R$_1$ | R$_2$ | R$_3$ | R$_4$ | R$_5$ |
|---|---|---|---|---|---|
| 2 | —CHO | H | H | Cl | —OAc |
| 3 | —CHO | H | H | Br | H |
| 4 | —CHO | H | H | H | H |
| 5 | —CHO | H | CH$_3$CO— | Cl | H |
| 7 | —CHO | —CH$_3$ | —CH$_3$ | Cl | H |
| 8 | —CHO | CH$_3$CO— | —CH$_3$ | Cl | H |
| 9 | —CHO | —CH$_3$ | CH$_3$CO— | Cl | H |
| 10 | —CHO | —CH$_3$ | H | Cl | H |
| 12 | —CHO | H | allyl | Cl | H |
| 20 | —CHO | H | benzoyl | Cl | H | compounds of formula (2)

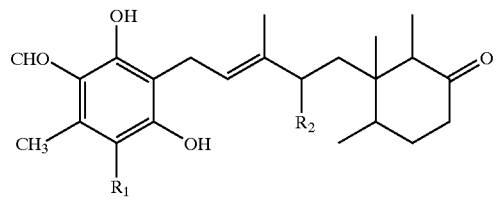

wherein

| # | R$_1$ | R$_2$ |
|---|---|---|
| 22 | Cl | H |
| 23 | H | H |
| 24 | Cl | —OH |
| 25 | Cl | —OAc | a compound of formula (3)

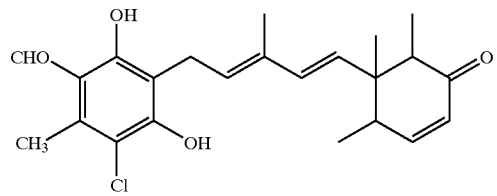

a compound of formula (4)

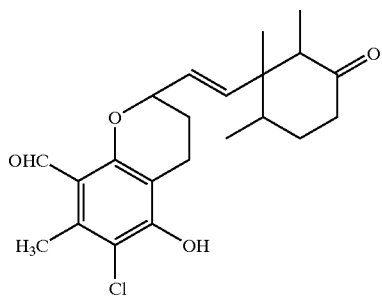

a compound of formula (5)

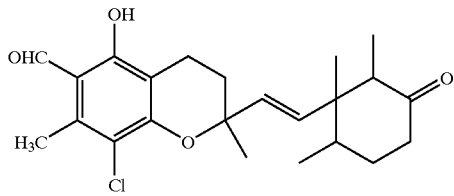

compounds of formula (6)

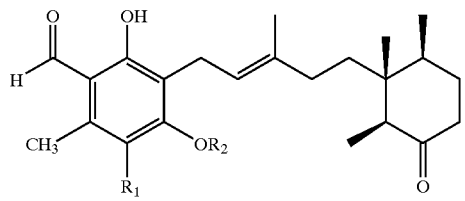

wherein

| # | R$_1$ | R$_2$ |
|---|---|---|
| 29 | Cl | H |
| 30 | Cl | —CH$_3$ |
| 31 | Cl | CH$_3$CO— |
| 32 | H | H |
| 33 | H | —CH$_3$ |
| 34 | H | CH$_3$CO— | and compounds of formula (7)

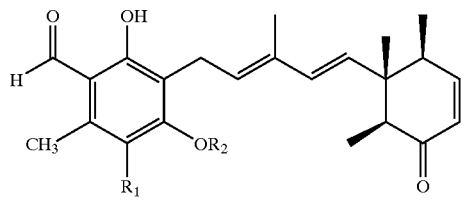

wherein

| # | R$_1$ | R$_2$ |
|---|---|---|
| 35 | Cl | H |
| 36 | Cl | —CH$_3$ |

-continued

| # | R$_1$ | R$_2$ |
|---|---|---|
| 37 | Cl | CH$_3$CO— |
| 38 | H | H |
| 39 | H | —CH$_3$ |
| 40 | H | CH$_3$CO— | a pharmaceutically acceptable salt thereof, and wherein said compound capable of acting as a retinoid X receptor ligand is in fine particle or amorphous form.

7. A method according to claim 1, wherein said compound capable of acting as a retinoid X receptor ligand is selected from the group consisting of:

compounds of formula (1)

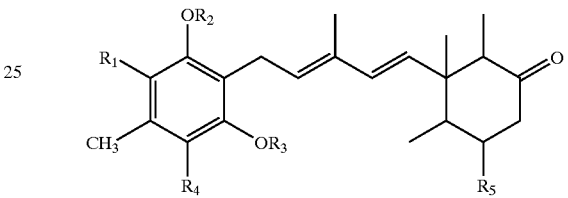

wherein

| # | R$_1$ | R$_2$ | R$_3$ | R$_4$ | R$_5$ |
|---|---|---|---|---|---|
| 2 | —CHO | H | H | Cl | —OAc |
| 3 | —CHO | H | H | Br | H |
| 4 | —CHO | H | H | H | H |
| 5 | —CHO | H | CH$_3$CO— | Cl | H |
| 7 | —CHO | —CH$_3$ | —CH$_3$ | Cl | H |
| 8 | —CHO | CH$_3$CO— | —CH$_3$ | Cl | H |
| 9 | —CHO | —CH$_3$ | CH$_3$CO— | Cl | H |
| 10 | —CHO | —CH$_3$ | H | Cl | H |
| 12 | —CHO | H | allyl | Cl | H |
| 14 | —CHO | H | —CH$_2$COOH | Cl | H |
| 15 | —CHO | H | —(CH$_2$)$_2$COOH | Cl | H |
| 16 | —CHO | H | —(CH$_2$)$_3$COOH | Cl | H |
| 17 | —CHO | H | —(CH$_2$)$_4$COOH | Cl | H |
| 18 | —CHO | H | —CH$_2$COOCH$_3$ | Cl | H |
| 19 | —CHO | H | nicotinoyl | Cl | H |
| 20 | —CHO | H | benzoyl | Cl | H |
| 21 | —CHO | H | isonicotinoyl | Cl | H | and compounds of formulae (2)–(7).

8. A method according to claim 2, wherein said disease or condition which can be alleviated by the RXRL-dependent regulation of gene transcription is hypertension, cerebral angiopathy, arterial restenosis following percutaneous transluminal coronary angioplasty, or arteriocapillary sclerosis or arteriosclerosis in transplanted organs, wherein said compound capable of acting as a retinoid X receptor ligand is selected from the group consisting of:

compounds of formula (1)

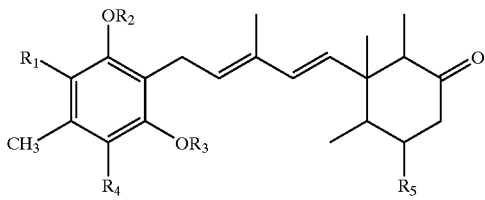

wherein

| # | R₁ | R₂ | R₃ | R₄ | R₅ |
|---|---|---|---|---|---|
| 2 | —CHO | H | H | Cl | —OAc |
| 3 | —CHO | H | H | Br | H |
| 4 | —CHO | H | H | H | H |
| 5 | —CHO | H | CH₃CO— | Cl | H |
| 7 | —CHO | —CH₃ | —CH₃ | Cl | H |
| 8 | —CHO | CH₃CO— | —CH₃ | Cl | H |
| 9 | —CHO | —CH₃ | CH₃CO— | Cl | H |
| 10 | —CHO | —CH₃ | H | Cl | H |
| 12 | —CHO | H | allyl | Cl | H |
| 14 | —CHO | H | —CH₂COOH | Cl | H |
| 15 | —CHO | H | —(CH₂)₂COOH | Cl | H |
| 16 | —CHO | H | —(CH₂)₃COOH | Cl | H |
| 17 | —CHO | H | —(CH₂)₄COOH | Cl | H |
| 18 | —CHO | H | —CH₂COOCH₃ | Cl | H |
| 19 | —CHO | H | nicotinoyl | Cl | H |
| 20 | —CHO | H | benzoyl | Cl | H |
| 21 | —CHO | H | isonicotinoyl | Cl | H | and compounds of formulae (2)–(7).

9. A method according to claim 1 or 2, wherein said compound capable of acting as a retinoid X receptor ligand is the compound of formula (1):

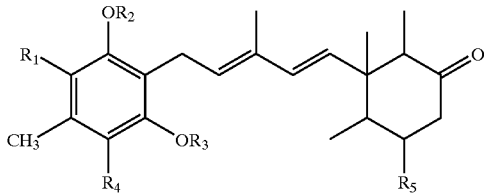

wherein

| # | R₁ | R₂ | R₃ | R₄ | R₅ |
|---|---|---|---|---|---|
| 6 | —CHO | H | —CH₃ | Cl | H | and
said additive is a synthetic aliphatic surfactant or a polymer substance soluble in organic solvents.

10. A method according to claim 1 or 2, wherein said compound capable of acting as a retinoid X receptor ligand is the compound of formula (1):

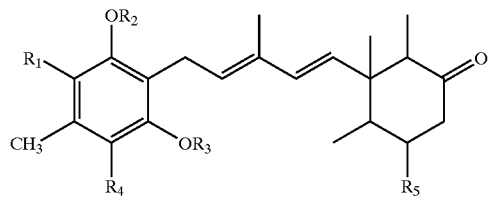

wherein

| # | R₁ | R₂ | R₃ | R₄ | R₅ |
|---|---|---|---|---|---|
| 6 | —CHO | H | —CH₃ | Cl | H, | and
said compound capable of acting as a retinoid X receptor ligand is in fine particle or amorphous form.

11. A method according to claim 4 wherein said compound capable of acting as a retinoid X receptor ligand is selected from the group consisting of:

compounds of formula (1)

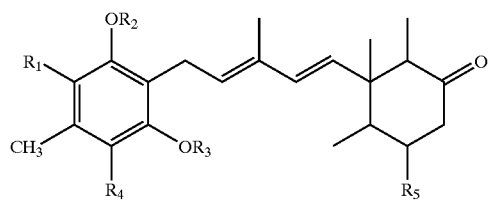

wherein

| # | R₁ | R₂ | R₃ | R₄ | R₅ |
|---|---|---|---|---|---|
| 1 | —CHO | H | H | Cl | H |
| 2 | —CHO | H | H | Cl | —OAc |
| 3 | —CHO | H | H | Br | H |
| 4 | —CHO | H | H | H | H |
| 5 | —CHO | H | CH₃CO— | Cl | H |
| 6 | —CHO | H | —CH₃ | Cl | H |
| 7 | —CHO | —CH₃ | —CH₃ | Cl | H |
| 8 | —CHO | CH₃CO— | —CH₃ | Cl | H |
| 9 | —CHO | —CH₃ | CH₃CO— | Cl | H |
| 10 | —CHO | —CH₃ | H | Cl | H |
| 11 | —CHO | H | CH₃CH₂— | Cl | H |
| 12 | —CHO | H | allyl | Cl | H |
| 13 | —CHO | H | butyl | Cl | H |
| 20 | —CHO | H | benzoyl | Cl | H | compounds of formulae (2)–(7).

12. A method according to claim 3 or claim 4 wherein said additive is a synthetic aliphatic surfactant or a polymer substance soluble in organic solvents.

13. A method according to claim 3 or claim 4 wherein said compound capable of acting as a retinoid X receptor ligand is in fine particle or amorphous form.

* * * * *